United States Patent [19]

Wang

[11] Patent Number: 4,870,974
[45] Date of Patent: Oct. 3, 1989

[54] APPARATUS AND METHOD FOR DETECTING HEART CHARACTERISTICS BY WAY OF ELECTRICAL STIMULATION

[75] Inventor: Xiangsheng Wang, Beijing, China

[73] Assignees: Chinese PLA General Hospital; CITIC Technology, Inc., both of Beijing, China

[21] Appl. No.: 175,514

[22] Filed: Mar. 31, 1988

[30] Foreign Application Priority Data

Sep. 30, 1987 [CN] China .................................. 87106622
Mar. 12, 1988 [CN] China .................................. 88101253

[51] Int. Cl.$^4$ .......................... A61B 5/04; A61N 1/36
[52] U.S. Cl. ............................... 128/700; 128/419 PG
[58] Field of Search ....... 128/419 P, 419PG, 419 PT, 128/696–697, 700, 702–705

[56] References Cited

U.S. PATENT DOCUMENTS

| | | | |
|---|---|---|---|
| 4,553,547 | 11/1985 | Keimel | 128/419 PG |
| 4,680,708 | 7/1987 | Ambos et al. | 128/703 X |
| 4,705,043 | 11/1987 | Imran | 128/419 PG |
| 4,708,142 | 11/1987 | DeCote, Jr. | 128/419 PT |
| 4,719,921 | 1/1988 | Chirife | 128/703 X |

FOREIGN PATENT DOCUMENTS

8520176.5 4/1985 China .

*Primary Examiner*—Francis Jaworski
*Attorney, Agent, or Firm*—Majestic, Parsons, Siebert & Hsue

[57] ABSTRACT

The apparatus and method of the present invention are used to detect the ECG and/or blood pressure (BP) waveforms and measure the R-R and Q-T intervals from the detected ECG signals, so as to determine the pulse structure of the heart stimulating signals, and to stimulate the heart. The heart is stimulated by the stimulating signals which includes a pacing pulse train applied to atrium for forming an artificial heart rhythm, and an inducing pulse train applied to ventricle for introducing ME or VT waveforms. By adjusting the time location and amplitude of the inducing pulses relative to the pacing pulses, the ME or VT waveforms are induced in the ECG signals. By detecting the ECG and/or BP waveforms, the ME or VT is identified and at the same time the heart stimulation is stopped. Then the induced ME or VT waveforms and the amplitude of the inducing pulse which induces the ME or VT waveforms are displayed and the ventricular fibrillation threshold is derived according to this amplitude.

18 Claims, 14 Drawing Sheets

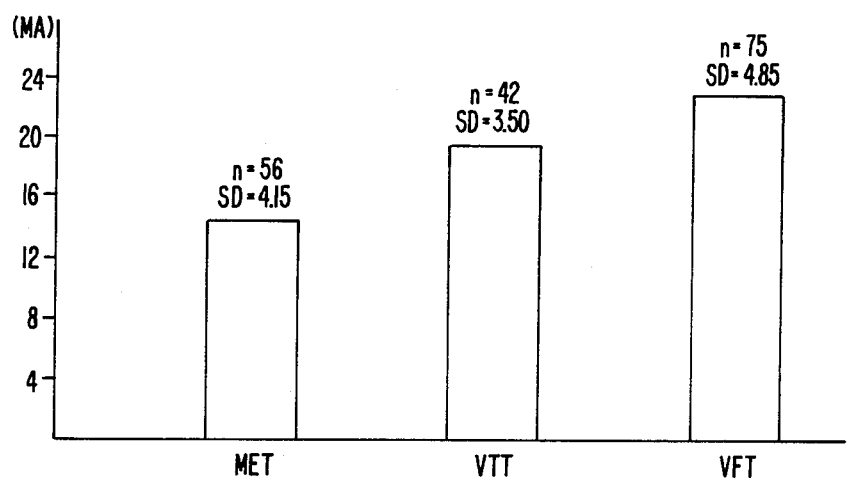
FIG._1.
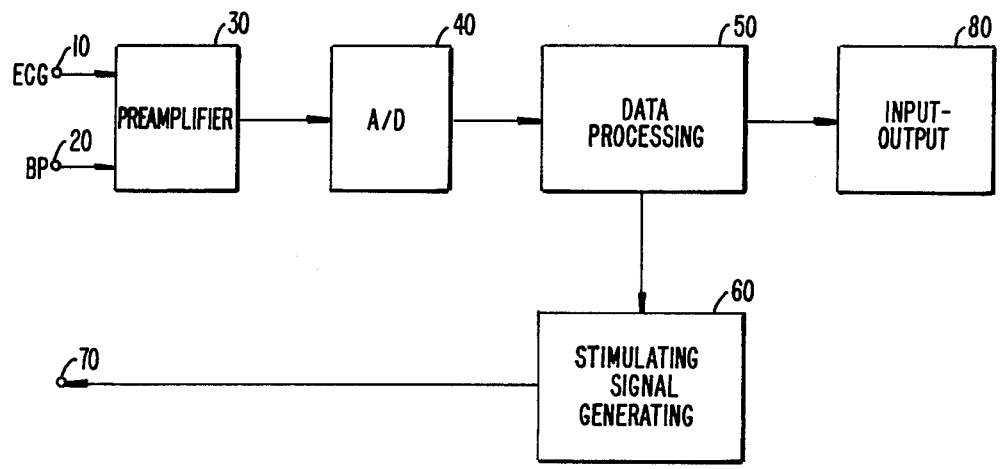
FIG._4.

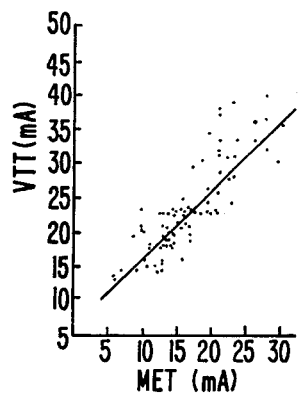
FIG._2A.
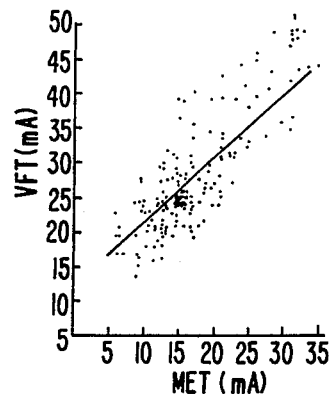
FIG._2B.
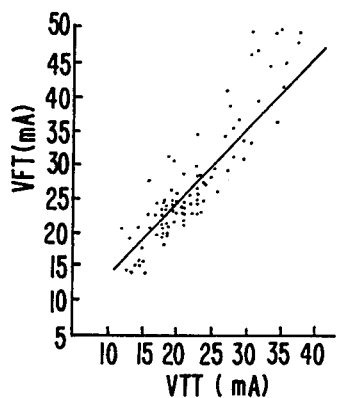
FIG._2C.
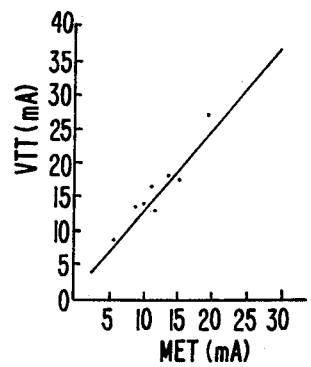
FIG._2D.
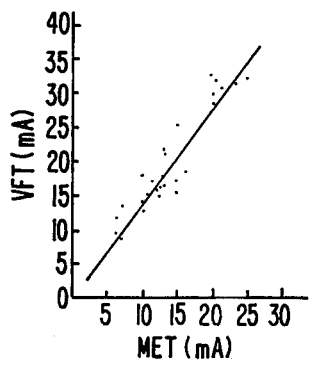
FIG._2E.
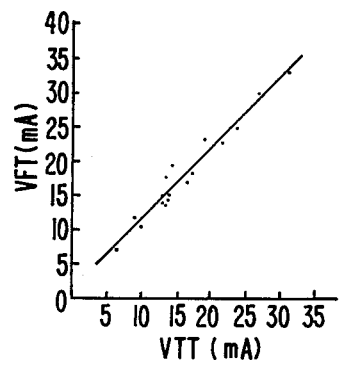
FIG._2F.

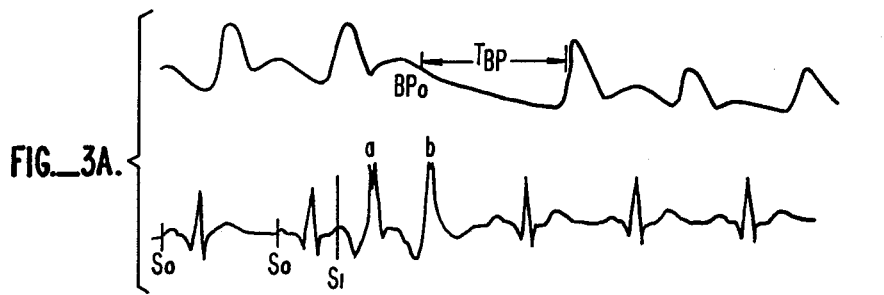
FIG._3A.
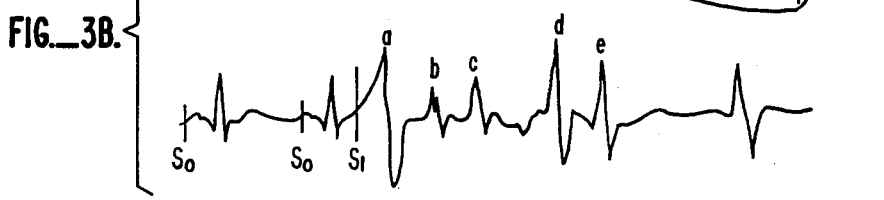
FIG._3B.
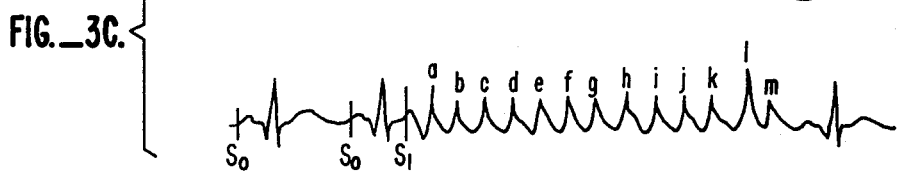
FIG._3C.
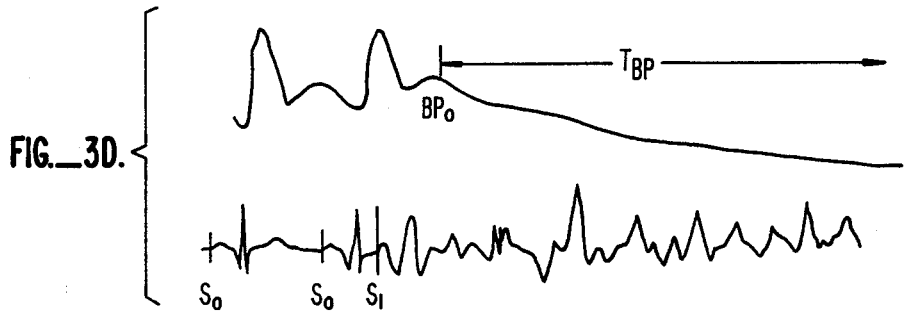
FIG._3D.

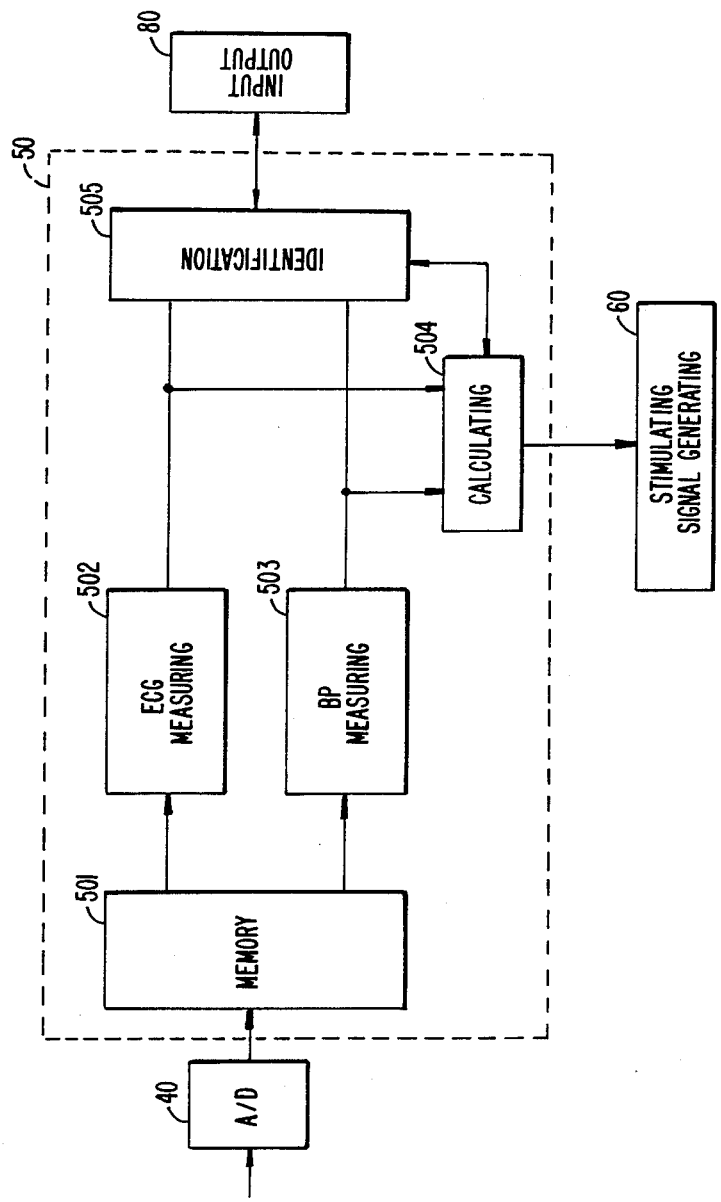
FIG._5.

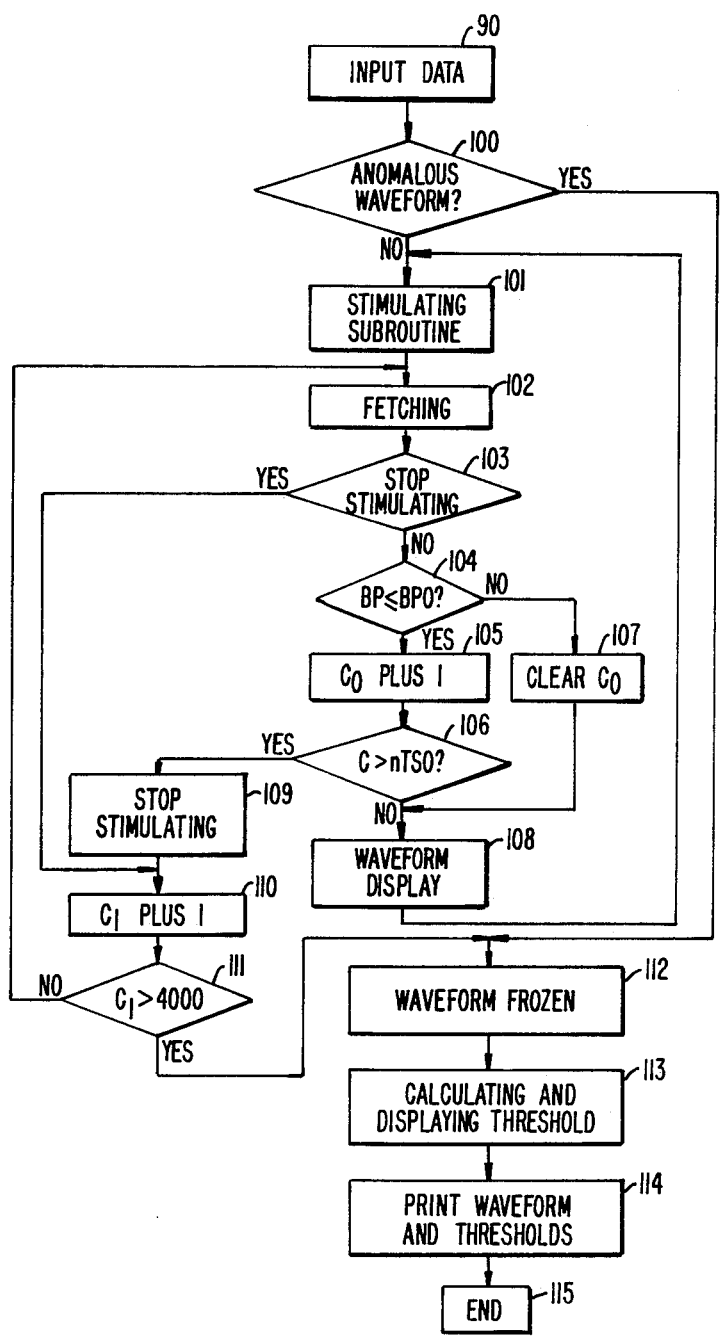
FIG._6.

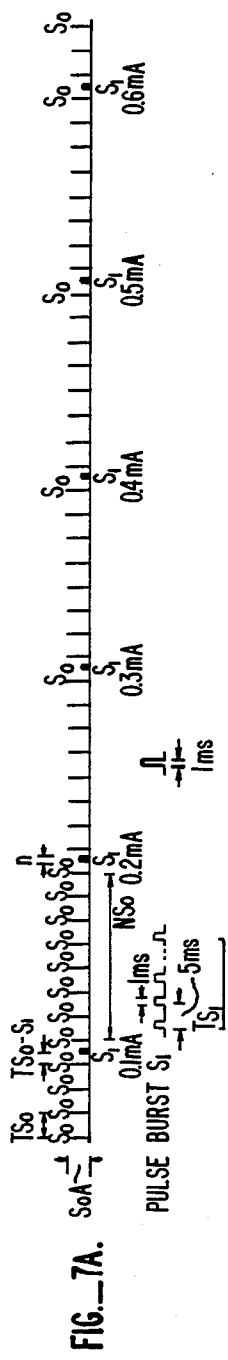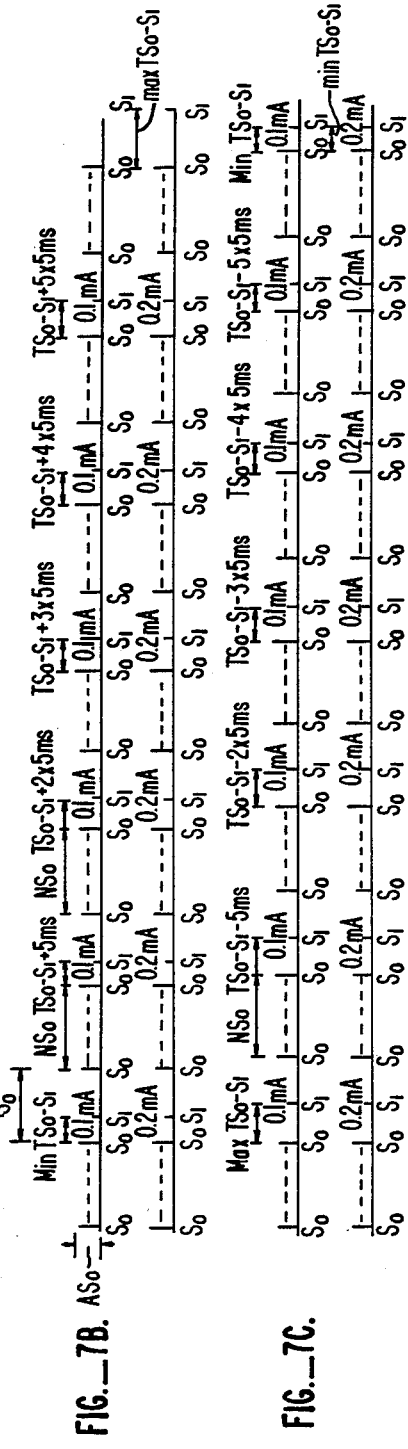
FIG._7A.
FIG._7B.
FIG._7C.

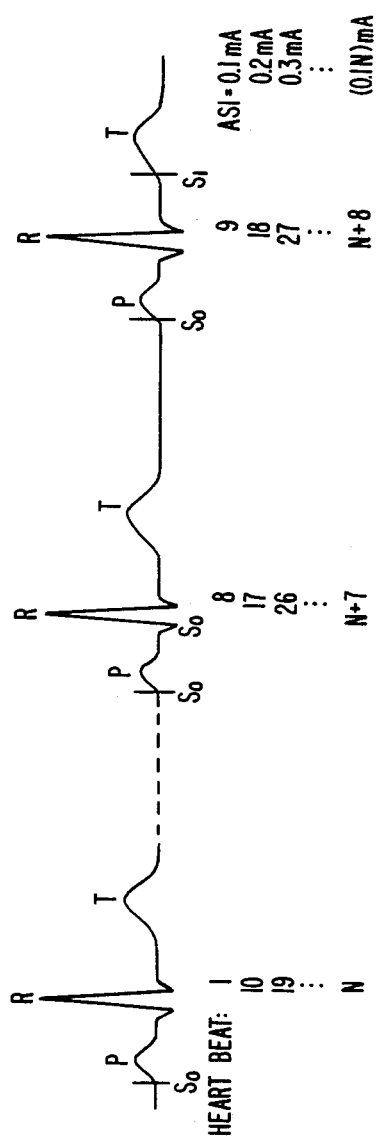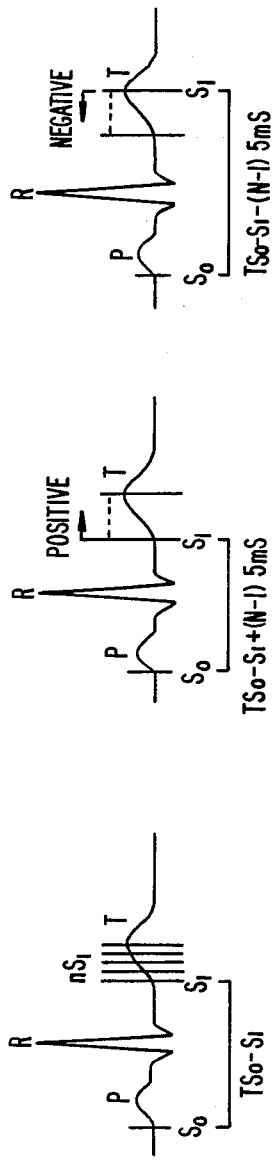
FIG._8.

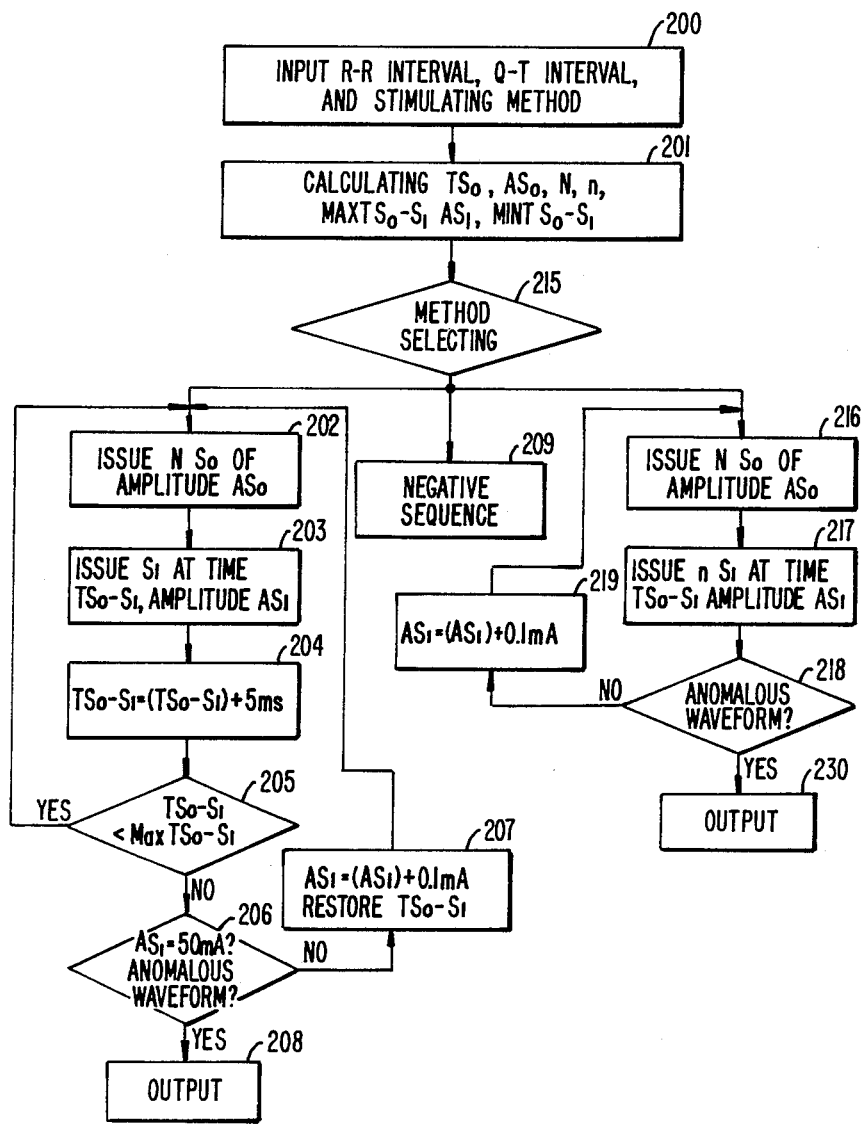
FIG._9.

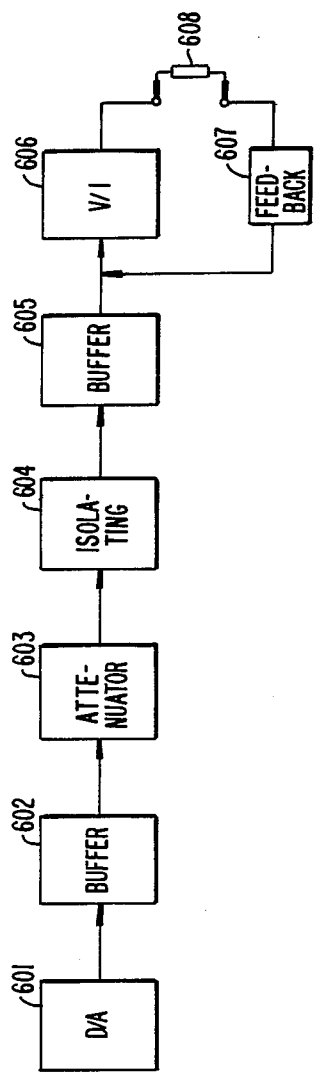
FIG._10.
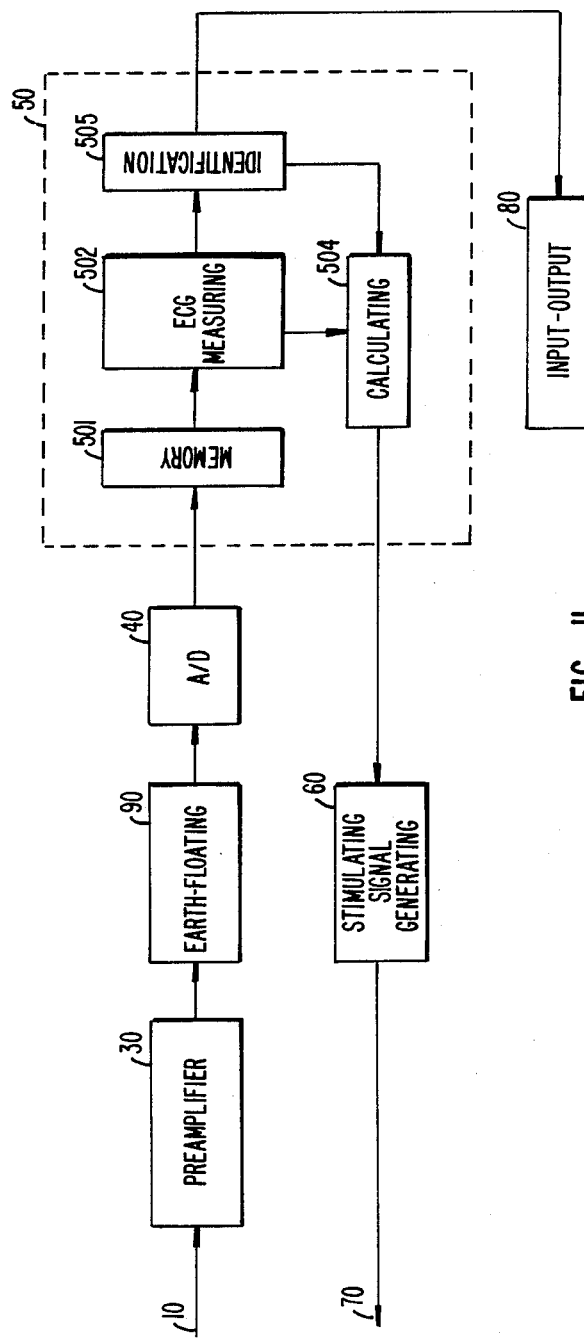
FIG._11.

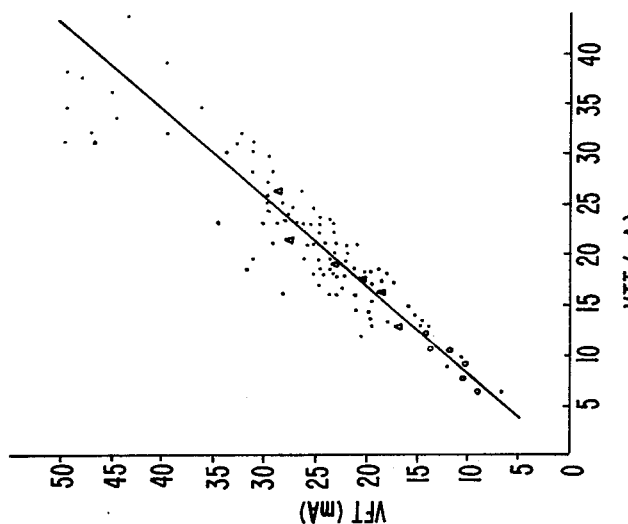
FIG._12C.
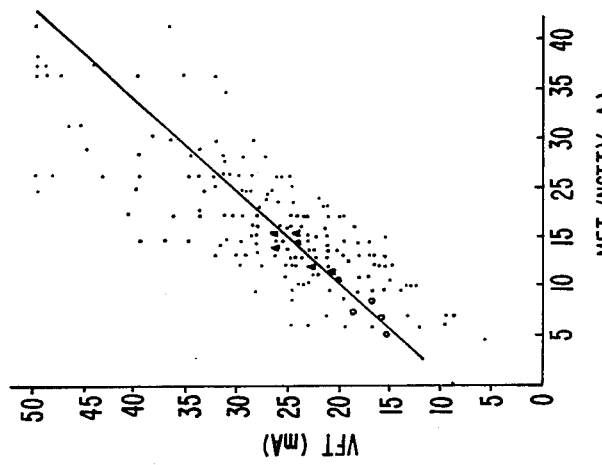
FIG._12B.
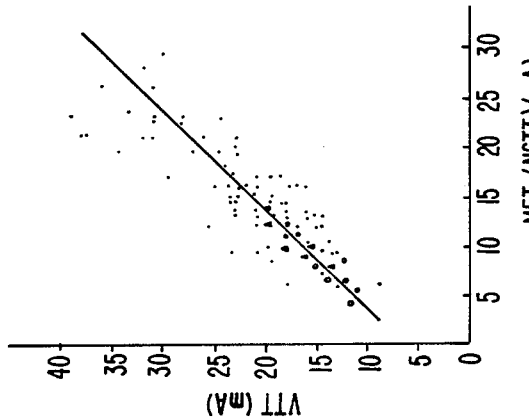
FIG._12A.

FIG._13A.
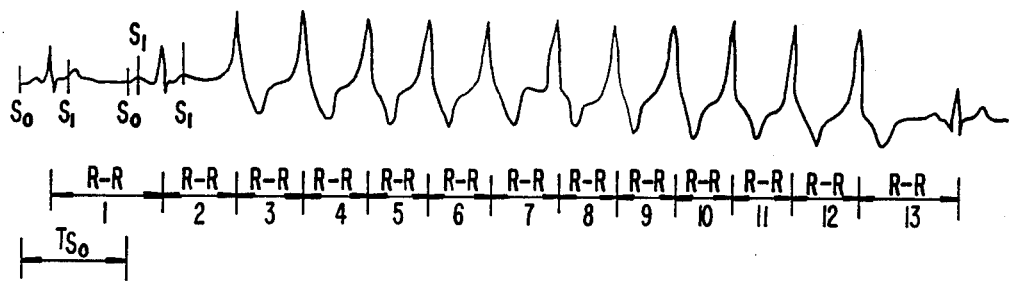
FIG._13B.
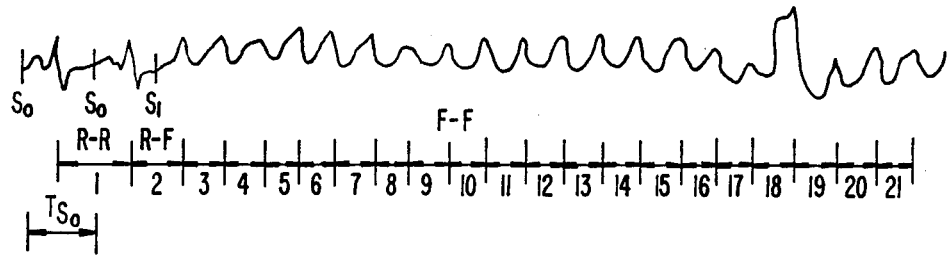
FIG._13C.

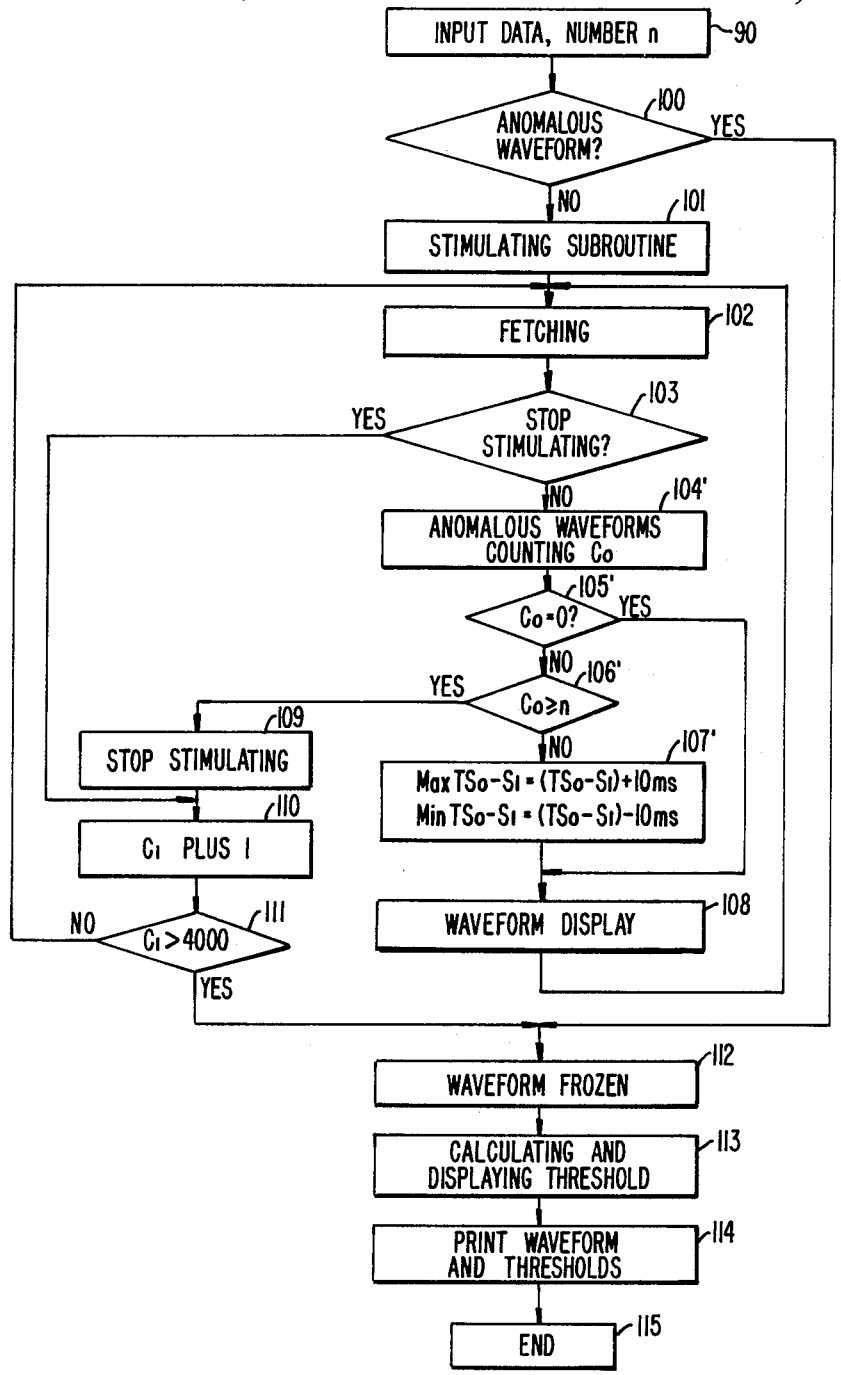
FIG._14.

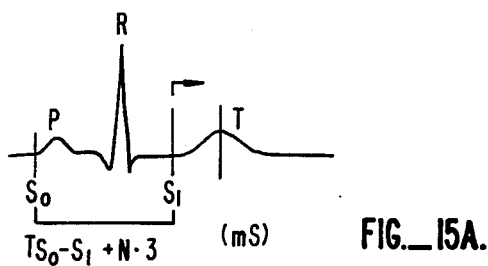
FIG._15A.
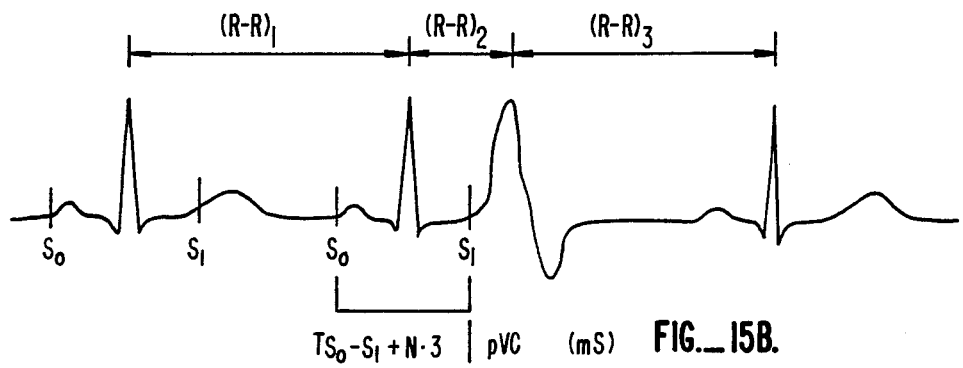
FIG._15B.
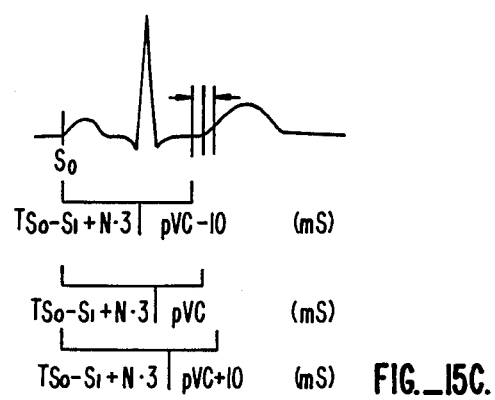
FIG._15C.

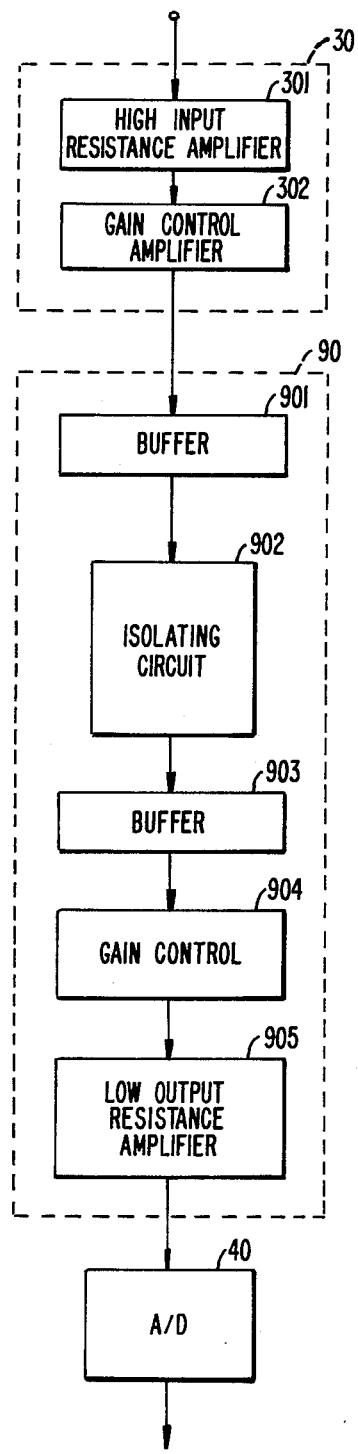
FIG._16.

APPARATUS AND METHOD FOR DETECTING HEART CHARACTERISTICS BY WAY OF ELECTRICAL STIMULATION

FIELD OF THE INVENTION

The present invention relates to an apparatus and method for detecting heart characteristics by way of electrical stimulation and, particularly, to an apparatus and method which applies stimulating signals of predetermined structure to the heart of a living body via stimulating electrodes and at the same time detects the change of the ECG signals of the stimulated heart, thereby to obtain the information about the heart characteristics.

PRIOR ART OF THE INVENTION

Sudden cardiac death is one of the most important reasons for the death of the adult and aged people, and of them about 25% have no symptoms at all beforehand. Therefore, the techniques for detecting heart characteristics and preventing the sudden cardiac death have always been a research field to which a great deal of attention has been paid by those involved in medical practice and research.

It is well-known that a heart beats rhythmically under the control of its own electrical signals, and the process of cardiac excitation of a normal person starts at the sinoatrial node, so the heart rhythm caused thereby is called the sinus rhythm. When the cardiac excitation starts from ventricles of the heart, it will be called the ventricular rhythm which is highly relevent to the sudden cardiac death. A wide and distorted QRS complex (with QRS duration>0.12 S) detected in ECG signals is called a premature ventricular contraction or PVC for short. When there are three or more succesive distorted QRS complexes, it will be called multiple extrasystoles or ME for short and it may also be called nonsustained tachycardia or NST for short. When there are ten or more successive distorted QRS complexes (with QRS duration>0.12 S, heart rate: 90–240 per minute), it will be called ventricular tachycardia or VT for short. When the QRST complexes in the ECG signals can not be identified and are replaced by irregular waveforms with a rate in the range of 250–500 per minute, it will be called ventricular fibrillation or VF for short. A great number of research reports have shown that: (a) the sudden cardiac death is caused by ventricular fibrillation; (b) there exists the cardiac-electric instability in the myocardium for any prospective victim of sudden cardiac death, and (c) the happening of PVC, ME (NST) or VT indicates the existence of the cardiac-electric unstability. In prior art, the concept of ventricular fibrillation threshold, or VFT for short, has been set up for the research of cardiac-electric instability, the concept of which is defined as the directly detected amplitude of the minimum stimulating current which induces ventricular fibrillation. This VFT may be used to indicate quantitatively the stability of the cardiac-electric activity of animal or human beings, so it is used as a quantitative indication for evaluating the possibility of the sudden cardiac death.

In detecting VFT, it is necessary to induce VF artificially and at present the most popular way for doing this in experiments is by electrical stimulation method. The method is done by applying electric current to myocardium during a specific period of the heart beat rhythm, namely the vulnerable period, to induce the incoordinate excitation of the adjacent myocardium fibers, which will cause ventricular fibrillation when reaching certain degree. The conventional electrical stimulation methods used in prior art are as follows:

1. Single square wave stimulating method. A single square wave pulse with certain amplitude and width is applied during the vulnerable period, and the strength of the stimulation is increased little by little until it reaches the minimum stimulating current for inducing VF and therefor its value is regarded as VFT. Since each time after the stimulating strength is increased, the diastolic duration of a heart beat has to be scanned so as to find out the vulnerable period, and since the current amplitude of the single pulse which at last induces VF is sometimes quite big, the detecting processes by way of gradually increasing the current amplitude is very time-consuming, while its advantage is that the start point of the vulnerable period is determined during the detection.

2. Sequential R/T stimulating method. Two or more properly arranged single pulses are sequentially applied to certain locations behind QRS complex and within the vulnerable period wherein a prior pulse has induced PVC waveform, then the current amplitude of the last stimulation for inducing VF is defined as VFT, usually three pulses are used. In this method, it is relatively easy to induce VF but the scanning for vulnerable period is still necessary, so it is still quite time-consuming.

3. Pulse burst stimulating method. A burst of certain number of pulses (usually 8–14 successive pulses) is used for stimulation. Since such a pulse burst may certainly cover the vulnerable period to induce VF, there is no need of scanning the vulnerable period and the current amplitude which actually induces VF is relatively small, so the advantage of this method is its quick detection.

4. Continuous square wave stimulating or continuous AC stimulating method. With this method, the continuous square wave or AC signals are applied to myocardium at random, so there is no need for delay means used after the R wave of the ECG signal. However, this method causes a long time of stimulation and hence has more injury to the heart, as a result it is seldom used now.

The prior art multi-functioned caridac programmable stimulator (such as model 5325 manufactured by Medtronics of USA,) is popularly used in the clinical electro-physiological study. It performs noninvasive pacing to atrium via esophageal electrodes, or performs intracardiac pacing via intracardiac electrodes, to detect electrophysiological functions and parameters of the sino-atrial node, atrio-ventricular node, Purkinje's fibres and anomalous conduction pathways. These techniques are called electrophysiological stimulation or physiologico-electrical stimulation (EPS-PES) techniques.

It is well recognized in prior art that the ventricular fibrillation threshold (VFT), which is defined as the amplitude of minimum stimulating current for inducing ventricular fibrillation during the process of electric stimulation of the heart, is a criterion for quantitatively describing cardiac-electric stability. However, the prior art methods for detecting VFT are all very dangerous and used mainly for animal experiments. In addition, the prior art detecting methods are performed by manual manipulation with several or more than a dozen pieces of equipment in the whole detecting process, so it is difficult for those medical staff having no electronic background to work with these complicated and time-consuming methods in clinical practice. Furthermore, when the prior art methods are used in animal experiments, the physiological status of the tested animal changes during the relative long time of the detecting process, so the comparability of the data obtained during the process is jeopardized.

In prior art, it is possible to use the programmable stimulator and EPS-PES method in inducing ventricular tachycardia (VT), but the result of the induction can not be used to indicate the cardiac-electric stability quantitatively. On the other hand, this inducing method is not guaranteed to prevent the happening of the ventricular fibrillation during the stimulation process, so it can not prevent the dangers when used in clinical practice. Therefore, the detection of the cardiac-electric stability is still an unsolved problem in prior art because of the restrictions on method and technical means.

SUMMARY OF THE INVENTION

On the basis of the research achievements of the present invention, the present inventor, for the first time, puts forward the following new conceptions:

1. Premature Ventricular Contraction Threshold (PVCT): this is defined as the minimum stimulating current applied to myocardium that induces the ECG waveform of premature ventricular contraction.

2. Multiple Extrasystoles Threshold (MET), this is also called Nonsustained Tachycardia Threshold (NSTT) in clinical practice: this is defined as the minimum stimulating current applied to myocardium that induces the ECG waveform of multiple extrasystoles.

3. Ventricular Tachycardia Threshold (VTT): this is defined as the minimum stimulating current applied to myocardium that induces the ECG waveform of ventricular tachycardia.

On the basis of the detection results of the present invention, the present inventor, for the first time, puts forward the following conception that besides the prior art ventricular fibrillation threshold (VFT), the premature ventricular contraction threshold (PVCT), the multiple extrasystoles threshold (MET) or nonsustained tachycardia threshold (NSTT), and the ventricular tachycardia threshold (VTT) may all be used to describe the cardiac-electric stability quantitatively. It is further shown by the detection results of the present invention that the actually detected values of the above-mentioned thresholds (PVCT, MET (NSTT), VTT and VFT) are increasing one by one, and it makes no difference whether they are detected in the normal myocardium or in the ischemic one, the detected thresholds are all highly correlated. Accordingly, it is proved by the detection results of the present invention that the dangerous VFT detection in prior art may now be replaced by the simple and safe detection of the PVCT, MET (NSTT), or VTT for the quantitative and reliable description of the cardiac-electric stability, and at the same time the VFT of the subject can be calculated according to his or her detected PVCT, MET (NSTT) or VTT.

For the safe and accurate detection of PVCT, MET (NSTT) and VTT, the present invention is furnished with specifically coded stimulating pulse trains which include both pacing pulses for forming artificial heart rhythm and inducing pulses for causing PVC,ME or VT. By adjusting the number, interval and amplitude of the pacing pulses, the heart under detection is made to beat according to an artificial heart rhythm, then the scanning of vulnerable period is made to this heart rhythm by applying the inducing pulses to each of the vulnerable period in a gradually increased amplitude and at the same time detecting the happening of PVC, ME (NST) or VT in the ECG and blood pressure (BP) signals, so that the PVCT, MET (NSTT) and VTT of the detected heart can be identified accurately and safely.

It is further shown by the detection results of the present invention that when there is occurrence of PVC, ME (NST), VT or VF in the heart rhythm, the value of real time blood pressure will be lower than that of the diastolic BP value under the normal heart rhythm; the longer the time duration of PVC, ME (NST), VT or VF is, the longer the time duration of the real time blood pressure below the normal diastolic blood pressure will be; and the value of the real time blood pressure will recover to the normal level only after there is a recovery of the normal sinus rhythm. Therefore, when PVC, ME (NST), and VT are identified by ECG analysing, the value of real time blood pressure may be used to verify such an identification, so as to avoid and prevent the inaccuracy of the threshold detection caused by noise and interference during the ECG analysis.

The first embodiment of the apparatus for detecting heart characteristics according to the present invention comprises: a plurality of ECG detecting electrodes, which may be any of the conventional ones; a blood pressure sensor, which may be artery catheter sensor, Doppler blood pressure sensor or any other sensor for transforming blood pressure (BP) signal into electrical signal; a preamplifier circuit for amplifying the ECG and BP signals detected by the ECG electrodes and BP sensor and providing parallel multiplex output; an A/D convertor for converting the multiplex output of the preamplifier circuit into multi-channel digital signals; a data processing unit which processes the multi-channel digital signals to generate control signals for heart stimulation; a stimulating signal generating unit which generates, under the control of of the output signal of the data processing unit, cardiac stimulating pulse trains; introcardiac electrodes which are introduced, via a catheter, into heart chambers to apply the cardiac stimulating pulse trains to the heart; and an input-output device for displaying said processed results provided by the data processing unit; wherein when the stimulating pulses are applied to the heart, the ECG electrodes and BP sensor monitor simultaneously the changes of heart characteristics under effects of the stimulating pulses. Then the data processing unit performs real time identification of the detected signals and, upon the identification of the PVC, ME (NST) or VT signals, the unit provides instructions to the stimulating signal generating unit to stop stimulating and sends the results of the identification to the output device for simultaneous displaying. By using the first embodiment of the apparatus for detecting heart characteristics according to the present invention, the PVCT, MET (NSTT), and VTT may be detected safely, automatically and accurately, and the VFT may be derived therefrom for the use of clinical practice and scientific research.

The method for detecting heart characteristics by using the first embodiment of the apparatus according to the present invention comprises the steps as follows:

a. detecting ECG and BP waveforms via conventional ECG detecting electrodes and BP sensor;

b. calculating real time heart rate according to the detected ECG signals;

c. generating a pacing pulse train with a frequency higher than the heart rate according to the above calculation, and generating an inducing pulse train at sequentially spaced apart time locations corresponding to the above pacing pulse train with gradually increased amplitude, so as to form a cardiac stimulating pulse train;

d. applying the cardiac stimulating pulse trains, via intracardiac electrodes, to the heart chambers;

e. detecting the real time changes of the ECG and BP signals under the effects of the above pulse trains;

f. performing real time analysis of the ECG and BP signals to identify ME (NST) or VT waveform;

g. stopping the electric stimulation applied to the heart upon the identifying of the ME (NST) or VT waveform; and h. displaying on an output device the identified ME (NST) or VT waveform, its corresponding BP waveform, and the amplitude of the inducing pulse which induces the waveforms, then deriving the VFT therefrom.

The second embodiment of the apparatus for detecting heart characteristics according to the present invention comprises: a plurality of ECG detecting electrodes of any conventional structure; a preamplifier circuit for amplifying the ECG signal detected by the ECG electrodes and providing the same as output; a preamplifier earth-floating circuit for keeping the detecting process from the interference of the stimulating process; an A/D convertor for converting the ECG output into digital signals; a data processing unit which processes the digital signals to generate control signals for heart stimulation; a stimulating signal generating unit which generates, under the control of the output signal of the data processing unit, cardiac stimulating pulse trains; heart stimulating electrodes which may be either introduced, via a catheter, into heart chambers, or introduced into esophagus to apply the cardiac stimulating pulse trains to the heart; and an input-output device for displaying the processed results provided by the data processing unit; wherein when the stimulating pulses are applied to the heart via the cardiac catheter or esophagus. The ECG electrodes detect the changes of heart characteristics under the effects of the stimulating pulses. The data processing unit performs real time identification of the detected ECG signals. Upon the identification of the PVC waveform, the unit restricts the scanning range of the stimulating pulse for the vulnerable period, then goes on increasing the amplitude of the stimulating pulses until the waveform of the ME (NST) or VT is induced. At this moment, the data processing unit provides instructions to the stimulating signal generating unit to stop stimulating and sends the identified results to the output device for simultaneous displaying. By using the second embodiment of the apparatus for detecting heart characteristics according to the present invention, the PVCT, MET (NSTT) and VTT may be detected quickly without BP detection, and then the VFT may be derived therefrom.

The method for detecting heart characteristics by using the second embodiment of the apparatus according to the present invention comprises the steps as follows:

a. detecting ECG waveforms via conventional ECG detecting electrodes;

b. calculating real time heart rate according to the detected ECG signals;

c. generating a pacing pulse train with a frequency higher than the above calculated heart rate, and determining the time locations and amplitudes of an inducing pulse train corresponding to the pacing pulse train so as to form cardiac stimulating pulse trains:

d. applying the pacing pulse train to atrium cordis and the inducing pulse train to ventricle;

e. detecting the PVC waveform in the ECG signals under the effects of the stimulating signals, locating the vulnerable period according to the location of the inducing pulse which induces the PVC waveform, and then increasing the amplitude of the inducing pulses within the vulnerable period;

f. performing real time analysis of the ECG signals to identify ME (NST) and/or VT waveform;

g. stopping the electric stimulation applied to the heart upon the identifying of the ME (NST) and/or VT waveform; and h. displaying on an output device the identified ME (NST) or VT waveform and the amplitude of the inducing pulse which induces the waveform, then deriving the VFT therefrom.

When the detection of heart characteristics is performed by using the second embodiment of the apparatus of the present invention and the method thereof, there is no need for BP detection and no need for artery puncture either. On the other hand, it is possible to replace the introcardiac stimulation, which is done by cardiac catheter, by the esophageal stimulation. Therefore, it relieves the subjects from the pain, the invasive injury and the dangers and also simplifies the medical staff's operation.

One object of the present invention is to provide an apparatus for detecting heart characteristics which artificially induce the ME (NST) and/or VT waveforms in ECG signals by specifically coded electric stimulating signals, and derive the ventricular fibrillation threshold (VFT) of the heart according to the amplitude of the stimulating pulse which induces the waveforms, so as to make a quantitative detection of the cardiac-electric stability.

Another object of the present invention is to provide a specifically coded electric stimulating pulse train which includes pacing pulses applied to atrium for evenly pacing the heart beat, and inducing pulses applied to ventricle once for several pacing pulses to induce ME (NST) and/or VT waveforms.

The frequency of the pacing pulses is slightly higher than the subject's heart rate while the location of each inducing pulse is moved a little after each pacing cycle, so as to scan the vulnerable period of the ECG signal. In addition, after each scan of the vulnerable period the amplitude of the inducing pulse will be increased by a small amount until it induces the ME (NST) and/or VT waveforms.

Yet another object of the present invention is to provide a method for detecting heart characteristics which induce the ME (NST) and/or VT waveform artificially by the above-mentioned stimulating pulse train, and derive the VFT of the detected heart according to the amplitude of the ventricular stimulating pulse which induces the waveform, so as to make a quantitative detection of the cardiac-electric stability.

The cardiac-electric stability is quantitatively detected without causing ventricular fibrillation by using the apparatus, electric stimulating pulse train and detecting method according to the present invention, so as to improve the safety of the detecting process significantly, Therefore, the detection can be performed for both animals and human beings in conscious state and under normal conditions, and it may be widely used in clinical practice and scientific research.

The apparatus of the present invention is fully automatically controlled during the whole detection process, and hence the detection processing is quick, simple and safe, and any medical staff without special training will be able to handle and use the apparatus.

By applying specifically coded stimulating signals to heart and simultaneously detecting the real time waveform of the blood pressure, the apparatus and method of the present invention can make the detected results with better accuracy and comparability, only to make these results more useful in clinical practice and scientific research.

The apparatus and method of the present invention may be used to predict the possibility of the sudden cardiac death of a patient, so it offers a new approach for the diagnosis of diseases in clinical practice.

The apparatus and method of the present invention may be used in general survey of ECG thresholds of a population, so it may offer quantitative criteria for preventing heart diseases and for selecting proper pacemaker or defibrillator for patients with heart disease.

The apparatus and method of the present invention may also be used to detect the effects of drugs on the ECG thresholds of animals and human beings, so it can be used by doctors as a reference in choosing drugs for patients, and it can be used in laboratory as well to provide quantitative criteria in the animal experiments of the pharmaceutical analysis. For the same reasons, the apparatus and method of the present invention may be widely used in the experiments of physiology, pharmacology, environmental protection, prevention of accupational diseases, and biological study.

The first embodiment of the apparatus of the present invention was exhibited in the 15th International Exhibition of Inventions and New Techniques of Geneva, on Apr. 4, 1987 and was awarded a gold medal and a grand prize.

The other objects, features, advantages and utilities of the present invention will become more apparent in the following detailed descriptions of the preferred embodiments of the present invention in combination with the accompanying drawing.

BRIEF DESCRIPTION OF THE DRAWINGS

FIG 1. shows the relationship between the MET (NSTT) VTT and VFT detected by using the apparatus and method of the present invention;

FIGS. 2A–2F show the statistical distribution of the thresholds detected by using the apparatus and method of the present invention;

FIGS. 3A–3D show the ECG and BP waveforms of the PVC, ME (NST), VT̂ and VF detected by using the apparatus and method of the present invention;

FIG. 4 shows the illustrating block diagram of the first embodiment of the apparatus for detecting heart characteristics according to the present invention;

FIG. 5 shows the illustrating block diagram of the data processing unit 50 shown in FIG. 4;

FIG. 6 shows the flow chart of program for identifying ME/VT/VF waveforms in the ECG and BP signals executed by the identification unit 505 shown in FIG. 5;

FIG. 7 shows the coding structure of the caridac electric stimulating pulse train according to the present invention;

FIG. 8 shows the relationship between the ECG signals and the stimulating pulses;

FIG. 9 shows the flow chart for the coding of the cardiac electric stimulating pulse train executed by the calculating unit 504 shown in FIG. 5;

FIG. 10 shows the illustrating block diagram of the stimulating signal generating unit 60 shown in FIG. 4;

FIG. 11 shows the illustrating block diagram of the second embodiment of the apparatus for detecting heart characteristics according to the present invention;

FIGS. 12A–12C show the statistical distribution of the thresholds of the present invention;

FIGS. 13A–13C show the ECG waveforms of the ME (NST), VT and VF detected by using the second embodiment of the apparatus of the present invention;

FIG. 14 shows the flow chart of program for identifying PVC/ME/VT waveforms in the ECG signals executed by the identification unit 505 shown in FIG. 11;

FIGS. 15A–15C show the method for locating the ECG vulnerable period by way of PVC waveform identification performed by the second embodiment of the apparatus of the present invention; and FIG. 16 shows the theoretical block diagram of the preamplifier circuit 30 and earth-floating circuit 90 shown in FIG. 11.

DETAILED DESCRIPTION OF THE PREFERRED EMBODIMENTS

Referring to FIG. 1, there is shown the statistical averages of the MET (NSTT), VTT and VFT detected from the healthy people by using the apparatus and method of the present invention. It is shown in FIG. 1 the sample number n and the standard deviation SD of each average. It is known from the results shown in FIG. 1 that by increasing gradually the amplitude of the stimulating pulses, it will induce one by one the waveforms of ME, VT and VF in the ECG signals of the same subject.

FIGS. 2A–2F show the statistical distribution of the thresholds detected from the normal myocardium and ischemic myocardium by using the apparatus and method of the present invention, wherein each point represents the relationship between two thresholds detected from the same subject. FIG. 2A shows the statistical distribution of MET versus VTT detected from 91 cases of normal myocardium; FIG. 2B shows that of MET versus VFT detected from 163 cases of normal myocardium; FIG. 2C shows that of VTT versus VFT detected from 103 cases of normal myocardium; FIG. 2D shows that of MET versus VTT detected from 8 cases of ischemic myocardium, FIG. 2E shows that of MET versus VFT detected from 32 cases of ischemic myocardium; and FIG. 2F shows that of VTT versus VFT detected from 17 cases of ischemic myocardium. It is shown by the above statistic data that no matter whether it is for normal or ischemic myocardium, the three thresholds, MET (NSTT), VTT and VFT, are all highly correlative (with a correlation coefficient r in the range of 0.72–0.99, $P<0.01$). The recursive equations between the three thresholds are given in Table 1:

TABLE 1

|  | Normal Myocardium |
|---|---|
| MET/VTT | VTT = 1.4265 + 0.9719 MET |
|  | MET = 0.1419 + 0.6675 VTT |
| MET/VFT | VFT = 2.4709 + 0.9222 MET |
|  | MET = 0.3116 + 0.5560 VFT |
| VTT/VFT | VFT = 0.3617 + 1.1137 VTT |

TABLE 1-continued

|  | VTT = 0.7211 + 0.6980 VFT |
|---|---|
|  | Ischemic Myocardium |
| MET/VTT | VTT = 0.2448 + 1.1921 MET |
|  | MET = 0.1309 + 0.7346 VTT |
| MET/VFT | VFT = 0.0082 + 1.3995 MET |
|  | MET = 0.4741 + 0.5860 VFT |
| VTT/VFT | VFT = 0.3209 + 1.0161 VTT |
|  | VTT = 0.9413VFT − 0.1517 |

It is shown by the equations in Table 1 that according to whether there is ischemia in the myocardium, the different equations may be selected to derive VFT from MET or VTT, so as to avoid performing the highly dangerous VFT directive detection. The reliability of the derived results has have been proven by experiments.

Referring to FIGS 3A–3D, there are shown the ECG signals and their corresponding BP signals with PVC, ME (NST), VT and VF real time waveforms contained therein respectively detected by using the apparatus and method of the present invention. In each of the figures, the abscissa represents time, the upper curve is the BP waveform while the lower curve is the ECG waveform. When there exists anomalous heart beats (such as ME (NST), VT or VF) during the rhythmic heart beat process, the blood pressure will be decreased correspondingly to a value lower than the diastolic BP at normal heart rhythm. Different types of anomalous rhythm correspond to different duration of BP decrease. In the order of ME (NST), VT and VF, their time duration for anomalous beats becomes longer and longer. Based on this phenemenon, the apparatus of the present invention makes the identification of the types of anomalous cardiac rhythm with the help of BP detection for the time duration when the real time value of BP is lower than the normal value of diastolic BP. Since the judgement in this BP identification is very simple and it is not adapted to the interference caused by the electric stimulating signals applied to the heart, this BP identification is easy to fulfil and highly reliable. FIG. 3A shows the PVC waveforms a and b and their corresponding BP decrease time Tbp, wherein BPo indicates the normal value of the diastolic BP. FIG. 3B shows the ME (NST) waveforms a–e and their corresponding BP decrease time Tbp which is longer than that of FIG. 3A. FIG. 3C shows the VT waveforms a–m and their corresponding BP decrease time Tbp which is significantly longer than that of FIG. 3B. FIG. 3D shows the VF waveforms and their corresponding BP decrease, if nothing is done at this situation, Tbp will last a long time and this will endanger the subject's life.

FIG. 4 shows the illustrating block diagram of the apparatus for detecting heart characteristics according to the present invention. In FIG. 4, numeral 10 indicates conventional ECG detecting electrodes which may be used for multi-lead (such as conventional 12 leads) ECG detection. Numeral 20 indicates a BP seosor which may be any conventional BP sensor, such as artery catheter sensor or Doppler BP sensor, etc. Numeral 30 indicates a preamplifier circuit which amplifies multiplex ECG signals and BP signals to provide parallel multiplex outputs. Numeral 40 indicates an A/D convertor which converts the parallel multiplex outputs from the preamplifier circuit 30 into multi-channel digital signals. The above ECG detecting electrodes 10, BP sensor 20, preamplifier circuit 30 and A/D convertor 40 are all known in prior art, so they will not be further described. Numeral 50 indicates a data processing unit, 60 indicates a stimulating signal generating unit; 70 indicates intracardiac electrodes, such as conventional two-path cardiac catheter electrodes; and 80 indicates an input-output device. When the system is started to work, the multi-channel ECG and BP digital signals are provided to the data processing unit 50 where these signals are processed and instructions are provided to the stimulating signal generating unit 60 according to the processed results. According to the instructions, the simulating signal generating unit 60 generates specifically coded stimulating pulse trains which are applied, via the stimulating electrodes 70, to right atrium and right ventricle, respectively. At the same time, detecting electrodes 10 and BP sensor 20 detect the ECG and BP signals from the heart under stimulation, and the data processing unit 50 performs waveform identification on the detected results until the waveform of ME (NST) or VT is identified. Then instructions are immediately sent to the stimulating signal generating unit 60 to stop the heart stimulation while the waveform of ME(NST) or VT and the amplitude of the stimulating pulse which induce the waveform are displayed by the input-output device 80 and the VFT is derived therefrom.

FIG. 5 shows the block diagram of the data processing unit 50 shown in FIG. 4. In FIG. 5, numeral 501 indicates a memory unit which stores the multi-channel data for further processing. Numeral 502 indicates an ECG measuring unit which fetches multi-lead ECG data from the memory unit 501 and performs the measurements of the parameters such as R-R interval, Q-T interval and the shifting of ST segment, so as to generate ECG measuring signals. Since all these measurements are known in the prior art, they will not be further described. Numeral 503 indicates a BP measuring unit which fetches BP data from the memory unit 501 and measures the waveform, the systolic and diastolic BP value from the data to generate BP waveform measuring signals. Numeral 504 indicates a calculating unit which inputs the ECG measuring signals from the ECG measuring unit 502 and BP measuring signals from the BP measuring unit 503, then calculates the parameters for the cardiac stimulating pulse train according to these input signals and sends the calculated parameters to the stimulating signal generating unit 60 as the operating instructions. Numeral 505 indicates an identification unit which inputs ECG measuring signals from ECG measuring unit 502 and BP measuring signals from BP measuring unit 503. All the input signals are first performed ME (NST) or VT identification in unit 505 to eliminate the case that the subject has anomaolous ventricular rhythm before the stimulating signals are applied, the stimulating signals are applied to those having normal heart rhythm. The ME (NST) or VT waveforms are identified according to the change of the ECG and BP signals under the effects of the heart stimulating signals, and upon the identification of the waveforms of the anomalous heart beats, instructions for stopping heart stimulating are sent to the calculating unit 504, from which the amplitude of the stimulating pulse which induces the anomalous heart beats is inputted at the same time, then the waveforms of the induced anomalous heart beats and the measured or derived values of MET, VTT and VFT are displayed by the input-output device 80.

FIG. 6 shows the flow chart of the program for identifying ME/VT/VF waveforms in ECG and BP signals executed by the identification unit 505 shown in FIG. 5.

At first, the measured data of ECG and BP waveforms are provided at step 90; then at step 100, the waveform of ME or VT is judged, if there is, the program enters step 112, no electric stimulating will be performed, if there is no anomalous waveform of ME or VT, it enters step 101. At step 101, instructions for starting heart stimulation are issued to the calculating unit 504; the measured data (BP, R-R interval, Q-T interval, ST shift) are inputted from the ECG measuring unit 502 and BP measuring unit 503 at step 102; then it is judged at step 103 whether there are instructions issued to the stimulating signal generating unit 60 for stopping heart stimulation. If no instructions are issue it enters step 104 to judge whether the real time BP value is less than the normal diastolic BP value. If this is not the case, it enters step 107 to clear counter Co, enters step 108 to display ECG and BP waveforms, and then returns to step 101. If the judgement in step 104 is yes, it enters step 105 to increment counter Co by 1, and then judge the time duration of the BP decrease at step 104. If the duration is less than a predetermined value, it displays ECG and BP waveform at step 108 and returns to step 101. If the duration of the BP decrease is larger than the predetermined value, instructions are issued to the stimulating signal generating unit 60 to stop heart stimulation at step 109. Then it enters step 110. If the judgement at step 103 is yes, it enters step 110, and then enters step 111 to fetch enough data points about the waveform of anomalous heart beats and displays the same at step 112. The MET, VTT and VFT are calculated and displayed according to the identified waveforms of anomalous heart beats at step 113. After print step 114 the whole process ends. The calculation equations used at step 113 are shown in Table 1. Whether there is ischemia in the myocardium is determined on the basis of the ECG measurements of the shifting of ST segment performed in the ECG measuring unit 502, or it may also be determined by the operator according to the manual measurements made to the ECG signals before the heart stimulation is applied. Then the relevent information is keyed in to select proper equations in Table 1 for calculating VFT.

FIG. 7 shows the waveform of the stimulating pulse train generated by the stimulating signal generating circuit 60 under the control of the calculating unit 504 shown in FIG. 5. The stimulating pulse train of the present invention includes two channels of pulses having different effects, one of them is the pacing pulse applied to right atrium by intracardiac electrodes to form an artificial heart rhythm and make it even so that the stimulation may be done at selected locations of each heart beat period. In FIG. 7A, the pacing pulses are indicated by So, its period Tso is made less than a R-R interval, usually 50–80% of one R-R interval, so that the detection will not be influenced by the sinus heart rhythm. The amplitude of the pulse So is indicated by SoA which is adjustable in the range of 1-20 mA. The other channel of pulses are called inducing pulses applied to right ventricle by the same intracardiac electrodes to induce PVC, ME(NST) or VT waveforms. The inducing pulses shown in FIG. 7, are indicated as S1. In each heart beat period, there is an period of 20-40 mS in width located between the start point to peak point of T wave. This is the period during which a stimulating pulse applied to heart will most possibly cause ME (NST), VT or VF. Hence this period is given a medical term "vulnerable period". The inducing pulses should be selectively applied during this period.

For the safety and accuracy of the detection, the amplitude of the inducing pulses applied during the vulnerable period should be increased gradually with an increment of less than or equal to 0.1 mA, until the ME (NST) or VT is induced. Then the amplitude AS1, at this moment, is the MET or VTT accordingly. Because of the individual differences, the location and width of the vulnerable period are different from person to person. In order to selectively cover this vulnerable period by inducing pulses, the present invention provides the following methods.

1. Pulse burst method. Referring to FIG. 7A, the pacing pulses So are first used to make the heart rhythm even, then after N pacing pulses So, a burst of n inducing pulses S1 with an amplitude of 0.1 mA is inserted, the interval between the Nth So and the first pulse S1 in the burst is Tso-s1. According to the detected Q-T interval, the pulse burst S1 may be applied to selectively cover the range between the start point and the peak point of the T wave. In this way, it is guaranteed that at least one S1 is applied to the heart during the vulnerable period. If ME or VT is not induced by the first pulse burst S1, the second pulse burst S1 is applied in the same way after another N pulses of So, but the amplitude of S1 is increased to 0.2 mA. This process continues until the waveform of ME (NST) or VT is induced. If the amplitude of pulse S1 has been increased to 50 mA but the waveform of ME or VT is not yet induced, the stimulation process should be stopped and that means the subject's cardiac-electric stability is good. The interposing N pulses of So for each burst of S1 are used to eliminate the effects of the former S1 on the heart and to let the heart recover to its normal state. This N may be any of 1-10 but preferably 8. The width of each inducing pulse S1 is 1 mS and the interval between two adjacent S1 is 5 mS, the number of pulses S1 in each burst, that is n, is decided by the width of the range between the start point and the peak point of the T wave.

2. Sequence method. This method is different from the pulse burst method at the point that only one pulse S1, instead of a burst of n pulses, is applied for each time, then the second pulse S1 of the same amplitude is applied after N pulses So at a location moved 5 mS. After this is repeated for several times, it finishes the stimulation similar to that done by the first pulse burst in the above-mentioned pulse burst method. Then the amplitude of the pulse S1 is increased by 0.1 mA and the process is continued in the same way. By this method, it will take more time than by the pulse burst method, but the accuracy of the detection is improved because it avoids the effects of n pulses acted on myocardium. If after each cycle the pulse S1 is moved forward in the direction from the start point of T wave to its peak point, it will be called the positive sequence method (referring to FIG. 7B), while if pulse S1 is moved backward, it will be called the negative sequence method (referring to FIG. 7C). FIG. 8 shows in detail the relationship between pacing pulse So, inducing pulse S1 and ECG signals.

Referring to FIG. 9, there is shown the stimulating pulse coding program executed by the calculating unit 504 shown in FIG. 5, which program generates the pulse trains shown in FIG. 7. First, at step 200, signals detected by the ECG measuring unit 502 and the BP measuring unit 503 are inputted, including R—R interval, Q-T interval, the shifting of ST segment of the ECG signals, the BP waveform, the value of systolic BP, diastolic BP, etc, and also the information about the stimulation method selected by the operator. At step 201, parameters such as Tso, Aso, N, n, Max Tso-s1, Min Tso-s1, As1 are calculated or selected according to the above input data, wherein Tso equals to 50–80% of R—R interval; Aso is adjusted by the operator to set up an even heart rhythm. N is selected in the range of 1–10; n=Tr/5+1. Tr is one half of the T waves width in term of millisecond. Max Tso-S1 is the time from the start point of P wave to the peak point of T wave. Min Tso-s1 is the time from the start point of P wave to the start point of T wave; and As1 is assigned a value of zero at the beginning. At step 215 a stimulating method subroutine is selected according to the operator's key-in information. Steps 202 to 208 form the positive sequence method, step 209 represents the negative sequence method and steps 216 to 230 form the pulse burst method. The negative sequence method, step 209, is done by adjusting the calculation made in the subroutine of the positive sequence method. First, N pacing pulses So are applied to the heart of step 202; then at step 203, an inducing pulse S1 of amplitude As1 is applied at point Min Tso-S1. At step 204, the next inducing pulse S1 is applied with a delay time of 5 ms. Then it is judged at step 205 whether the whole vulnerable period has not yet been covered. If it is not, the program returns to step 202 to repeat the process until the whole period is covered. Then it enters step 206, wherein it is judged whether instructions for stopping heart stimulation have been received from the identification unit 505 (namely the waveform of ME (NST) or VT has been identified, as shown by stop 109 in FIG. 6). If they have not been received, it goes on to judge whether As1 is equal to 50 mA. If the answer is also no, it enters step 207 to increase the value of As1 by 0.1 mA and restore Tso-s1. Then the increased inducing pulse S1 is used for the next cycle to scan the whole vulnerable period. When the anomalous waveforms are identified or the amplitude As1 is increased to 50 mA, it will enter step 208 wherein the amplitude As1 is provided to the identification unit 505 as the PVCT, MET or VTT for deriving VFT. If the operator selectes the pulse burst method, the program will be executed from step 215 to step 216, wherein N pacing pulses So are issued. Then at step 217, a burst of n inducing pulses with a width of 1 mS and interval of 5 mS will be issued at time Min Tso-S1. At step 218, it is judged whether the anomalous waveforms are induced or whether the amplitude of the pulse S1 has reached 50 mA. If neither condition is met, it enters step 219 to increase the amplitude of pulse S1 by 0.1 mA, and to repeat the same process until the anomalous waveforms are induced or the amplitude reaches 50 mA. Then the amplitude As1 is provided to the identification unit 505 as the threshold.

Referring to FIG. 10, there is shown the block diagram of the stimulating signal generating unit 60 shown in FIG. 4. In FIG. 10, numeral 601 indicates a D/A convertor, such as a dual channel 12 bits D/A convertor having a converting level of 0–5 V, which converts the instruction signals for generating electric stimulating pulse train, provided by the calculating unit 504 shown in FIG. 5, into analog signals. Converter 601 then provides the same to an isolating circuit 604 via a buffer unit 602 for impedance matching and an attenuator 603 for level adjusting. The isolating circuit 604 is used to keep the stimulating electrodes earth-floated from the apparatus, so as to guarantee the subject's safety; then via another buffer unit 605 for impedance matching. The voltage signal from the buffer unit 605 is converted into current signal by V/I convertor 606 and applied to heart chambers through the intracardiac electrode 70 shown in FIG. 1. A feedback circuit 607 is used to keep a constant current output from the intracardiac electrodes, which are not affacted by the cardiac resistance, so as to guarantee an accurate detection of the thresholds. In FIG. 10, numeral 608 represents the cardiac resistance, on which the stimulating signal is applied via the electrodes 70 shown in FIG. 1. The USCI intracardiac electrodes of model 006042 6F, which is commercially available, may be used in the invention. There are two pairs of electrodes, one of them may be used to apply pacing pulses So to the atrium while the other pair may be used to apply inducing pulses S1 to the ventricle.

Referring to FIG. 11, there is shown the block diagram of the second embodiment of the apparatus for detecting heart characterictics according to the present invention. In FIG. 11, numeral 10 indicates electrodes for conventional ECG detection. Numeral 30 indicates a preamplifier circuit which amplifies ECG signals to provide ECG output. Numeral 40 indicates an A/D convertor which converts the analog ECG signals from the preamplifier circuit 30 into digital signals. The above ECG detecting electrodes 10, preamplifier ciecuit 30 and A/D convertor 40 form the detecting portion of the apparatus, the portion is similar to that shown in the first embodiment of the present invention, so they will not be further described. In this second embodiment, there is added an earth-floating circuit 90 which separates the detecting portion from the other parts of the apparatus to avoid the electrical interference to the detection caused by the other parts, in this way it guarantees a stable waveform of the detected ECG signals. A dash line block 50 indicates a data processing unit which comprises: a memory unit 501 for storing digitized detection data; an ECG measuring unit 502 which fetches ECG data from the memory unit 501 and measures the R—R interval and Q-T interval from the ECG data to provide an ECG measuring signal; a calculating unit 504 which calculates parameters for heart stimulation according to the ECG measuring signal provided by the ECG measuring unit 502 and provides the calculated parameters as the heart stimulation control signal to the stimulating program shown in FIG. 9; an identification unit 505 which inputs the ECG measuring signal from the unit 502, performs the ME (NST) and VT identification on the input signal to eliminate the situation that the subject has the ventricular heart rhythm before the stimulating signal being applied. Unit 505 issues the instructions for stimulating only if the subject having normal heart rhythm, then performs the PVC, ME (NST) and VT identification on the ECG signals detected when the stimulating signals have been applied to heart, and issues the instruction for stopping stimulation to the calculating unit 504 upon the identifying of the waveform of anomalous heart beats. At the same time unit 505 inputs the amplitude of the stimulating pulse which induces the anomalous heart beats, and then provides the waveforms of the anomalous heart beats and the detected and derived thresholds as output. The program flow chart excuted by the identification unit 505 is shown in FIG. 14. Numeral 60 indicates a stimulating signal generating circuit and numeral 70 indicates intracardiac electrodes which may be any conventional dual-channel intracardiac electrodes for introcardiac stimulation, or esophageal electrodes applying noninvasive stimulation to the corresponding locations of the atrium and ventricle. The circuit 60 and electrodes 70 form the stimulating portion of the apparatus which is similar to the portion in the first embodiment of the present invention (Refer to FIG. 10 and the description). In the second embodiment of the apparatus, the detecting portion 10 and 30, and the stimulating part 60 and 70 are separated from the processing part 50 by the earth-floating circuit 90, so that the three parts will not interfere with each other and the detection made thereby is accurate. The details of the earth-floating aircuit 90 is shown in FIG. 10. Numeral 80 indicates an input-output device for displaying the PVC, ME (NST) and VT waveforms identified by unit 505, the amplitude of the inducing pulse, and the ECG thresholds derived therefrom, and for inputting operating instructions and relevent information.

Referring to FIGS. 12A–12C, there are shown the statistical distributions of the thresholds detected from the persons of normal myocardium, ischemic myocardium, myocardiosis, and the survivors of the sudden cardiac death, wherein a small point represents the relationship of two thresholds detected from the same person of normal myocardium, a big point that of ischemic myocardium, a small triangle that of myocardiosis, and a small circle that of the survivor of the sudden cardiac death. FIG. 12A shows the statistical distribution of MET (NSTT) versus VTT detected from 91 cases of normal myocardium, 8 cases of ischemic myocardium, 6 cases of myocardiosis and 6 cases of sudden cardiac death survivors. FIG. 12B shows the statistical distribution of MET (NSTT) versus VFT detected from 164 cases of normal myocardium, 31 cases of ischemic myocardium, 6 cases of myocardiosis and 6 cases of sudden cardiac death survivors. FIG. 12C shows the statistical distribution of VTT versus VFT detected from 102 cases of normal myocardium, 17 cases of ischemic myocardium, 6 cases of myocardiosis and 6 cases of cardiac sudden death survivors. It has been proved by the statistical analysis of the above data that no matter in normal or ischemic myocardium, the ECG thresholds, MET (NSTT), VTT and VFT are all highly correlative with each other (with a correlative coefficient $r: 0.77–0.99$, $p < 0.01$). It is shown by the above statistical data that although the thresholds of the normal and ischemic myocardium are distributed in different area, they are all in agreement with the recursive equations given in Table 2:

TABLE 2

| thresholds | recursive equations |
| --- | --- |
| MET | MET = 0.2375 + 0.6512 VTT |
| VTT | VTT = 1.2936 + 0.9981 MET |
| MET | MET = 0.3543 + 0.5489 VFT |
| VFT | VFT = 1.7932 + 1.0816 MET |
| VTT | VTT = 0.6673 + 0.7060 VFT |
| VFT | VFT = 0.1349 + 1.1608 VTT |

As shown in Table 2, a subject's VFT may be derived from his detected MET (NSTT) or VTT by using the above equations, so as to avoid making the dangerous VFT detection.

Referring to FIGS. 13A to 13C, there are shown the ECG waveforms of the ME (NST), VT and VF detected by using the second embodiment of the present invnetion. In each of the figures, the abscissa represents time and the ordinate represents the amplitude of the ECG signals. The letter So denoted in figures indicates the pacing pulses applied to atrium by one pair of stimulating electrodes for forming an even artificial heart rhythm with a heart beat period of Tso. The letter S1 indicates the inducing pulses applied to ventricle by another pair of stimulating electrodes. By adjusting its location and increasing its amplitude, inducing pulse S1 may induce anomalous heart beats when applied within the vulnerable period (referring to FIG. 7 and its description). Under the effects of the pacing pulses So, the heart rhythm becomes very even and at this time the R—R interval equals to Tso which is the period of pulse So, such as the first R—R interval shown in FIG. 13A. When the ventricular heart beats are induced by the inducing pulse S1, the R—R interval of these anomalous ventricular heart beats is less than Tso, such as the second to the fourth R—R intervals shown in FIG. 13A. If, at this moment, application of the pacing pulses So and of the inducing pulses S1 to the heart is stopped, the heart will automatically recover to its normal rhythm, such as shown in FIG. 13A. After the fifth R—R interval, it recovers the normal heart rhythm denoted as the sixth to the ninth R—R intervals which are larger than the pacing pariod Tso. When the number n of the successive ventricular heart beats caused by the inducing pulse S1 meets the condition: $n < 3$ (namely there are less than three successive waveforms whose R—R interval being less than Tso), it is called premature ventricular contraction (PVC). If $3 \leq n \leq 9$, it is called multiple extrasystoles ME (or nonsustained tachycardia NST), such as shown in FIG. 13A. If $n \geq 10$, it is called ventricular tachycardia (VT), such as shown in FIG. 13B wherein the first R—R interval equals to Tso while the second to the twelfth R—R intervals are less than Tso. When the amplitude of the inducing pulse S1 is equal or beyond VFT, it will cause ventricular fibrillation whose R—R intervals are totally irregular and the heart rate is beyond 250 per minutes, such as shown in FIG. 13C, wherein the VF waveform is very irregular and the R—R interval is not definite. If this situation is not stopped quickly, it will endanger the subject's life. It is one of the purposes of the present invention to prevent VF during the detection.

FIG. 14 shows the flow chart of the program for identifying PVC/ME/VT waveforms in ECG signals excuted by the identification unit 505. It should be pointed out that many steps and numerals shown in FIG. 14 are similar to that shown in FIG. 6. The difference between the two programs is that in the program shown in FIG. 6, the anomalous heart beats are identified according to the BP decrease while in the program shown in FIG. 14 they are identified according to the change of ECG waveforms. The latter program is described as follows. At first, the measured data of ECG signals are provided at step 90; then at step 100, the waveform of ME (NST) or VT is judged. If the waveform is anomalous, the program enters step 112 which means that the subject's condition is bad and no electric stimulation will be performed. If there is no anomalous waveform of ME or VT, it enters step 101. At step 101, instructions for starting heart stimulation are issued to the calculating unit 504 referring to FIG. 9 and its description for the details); the measured data (R—R interval, Tso, the location of S1 within a R—R interval, and the amplitude of S1) are inputted from the ECG measuring unit 502 and the calculating unit 504 at step 102. Then it is judged at step 103 whether there are instructions issued to the stimulating signal generating unit 60 for stopping heart stimulation. If no such instructions have been issued, it enters step 104 to count the number of the anomalous ECG waveforms induced by the stimulating pulses. It should be pointed out that in order to avoid the interference to the ECG waveforms caused by stimulating pulses So and S1, the detected ECG signals are first filtered to eliminate the waveforms having a width less than 10 mS, so that the pulses So and S1 which have a width of about 1 mS (see FIG. 7) are filtered. Then the filtered ECG signals are searched for the waveforms having a base frequency of 17 Hz, so as to identify QRS complex. In this way, it is possible to avoid errors caused by judging R waves according to their amplitude. When the QRS complexes are identified, R—R intervals may be measured and compared with Tso to identify the number of anomalous ECG waveforms Co (with R—R interval less than Tso). At step 105', it is judged whether Co is zero. If Co is zero, it means no anomalous heart beat has been induced, and through step 108, it returns to step 102 for fetching new detected data and continue the process until it is judged at step 105' that Co is not zero. Then it enters step 106'. Since the amplitude of the inducing pulse S1 is increased gradually, the first anomalous waveform induced by S1 is usually a PVC which meets the condition: $0 < Co < 3$. When it is judged at step 106' that the number of anomalous waveforms Co is less than 3, it enters step 107' wherein the location of the inducing pulse which has induced PVC is fixed. Because a PVC has been induced, it means this S1 was applied within the ECG vulnerable period, so it may be used to determine the location of the vulnerable period within a ECG period and to send the information to the the heart stimulating subroutine executed by the calculating unit 504. At step 107', the scanning range for the ECG vulnerable period is restricted from the original range of 200 m S (from the start point to the peak point of T wave) to a new range of 20 m S, thereafter, the scanning for the vulnerable period is made more accurately and quickly, hence the stimulating process for inducing ME and VT is accelerated significantly. After step 107' is executed, PVC waveform is displayed and Co is cleared at step 108, then the program returns to step 102 to continue the same process until it is judged at step 106' that Co is larger than 3, which means ME (NST) or VT is induced. Next, at step 109, instructions for stopping heart stimulating are issued to the stimulating signal generating unit 60. Then, through steps 110 to 114, enough data points about the identified ME (NST) or VT waveforms are fetched and displayed on the output device, and the thresholds MET, VTT and VFT are calculated and displayed.

FIGS. 15A–15C show the method for locating the ECG vulnerable period by way of PVC waveform identification. FIG. 15A shows the scanning range from the start point of T wave to its peak point, usually this range is about 200 mS in width. There is somewhere within this range a vulnerable period of 20–40 mS in width, but its exact location for each particular subject can not be determined before the stimulating pulses applied threreon because of the individual differences and the fluctuation of the ECG signals per se. In order to locate this vulnerable period, one inducing pulse S1 is applied to the scanning range after each group of N pacing pulses So, according to the above-mentioned sequence method, and for each cycle of this stimulation, pulse S1, is moved 5 mS, so that the whole range is scanned after about 40 cycles (200 mS/5mS). Then the pulse S1 is increased 0.1 mA and the scanning process is repeated in the same way until the waveform of ME (NST) or VT is induced. FIG. 15B shows an improved method wherein the pulse S1 in the first R—R interval does not induce anomalous R wave but the pulse S1 in the second R—R interval induces a PVC waveform that means the second S1 is within the vulnerable period. In this improved method, the scanning process is not continued in the same way after ME (NST) or VT is induced, but at the moment when one or two PVC waveform is induced, the ECG vulnerable period is determined according to the location of the pulse S1, then a new scanning range is made from 10 mS before pulse S1 to 10 mS after it, in this way the original scanning range of 200 mS is narrowed down to a new scanning range of 20 mS. Since the amplitude of the S1 which induces PVC is much smaller than that of the S1 which induces ME or VT, the location of the vulnerable period is determined at a relatively early time in the above-metioned method. Then the pulse S1 with increased amplitude will be applied only to the determined vulnerable period until ME (NST) or VT is induced therein. In this way the detection is significantly accelerated by a more selective scanning of the vulnerable period. FIG. 15C shows the location of the vulnerable period determined by PVC identification for later stimulation. The pulse S1 applied to the heart thereafter will be restricted to this narrow range until ME or VT is induced.

Referring to FIG. 16, there is shown the block diagram of the preamplifier circuit 30 and the earth-floating circuit 90 shown in FIG. 11. In FIG. 16, the dash line block 30 indicates the preamplifier circuit which comprises amplifier 301 of high input resistance which has a ground resistance larger than 1000 M ohm and a current leakage less than 1 uA; and a gain control amplifier 302 which controls the output of the amplifier 301 to a proper gain level. The dash line block 90 indicates an earth-floating circuit which comprises a buffer stage 901; an isolating circuit 902 which may be a photoelectric coupler; another buffer stage 903. Both buffer stages 901 and 903 are used for impedance matching with the isolating circuit 902. Block 90 also includes a gain control circuit 904 which is used to control the gain of the output of the isolating circuit 902; and a low output resistance amplifier 905 which has an output resistance of less than 100 ohms to avoid the interference from the load. Since the isolating circuit 902 is used in the second embodiment of the apparatus of the present invention for earth-floating connection of the detecting portion, it cooperates with the isolating circuit 604 (shown in FIG. 10) of the stimulating signal generating unit 60 to prevent the interference between the detecting and the stimulating portions and at the same time to guarantee the subject's safety. In this arrangement, the data processing unit 50 receives detected ECG signals of little interference which provides a very good condition for identifying PVC, ME and VT therefrom.

The apparatus and method of the present invention are described with reference to the two preferred embodiments, however, it is obvious that many modifications and rearrangements may be made by those skilled in the art without departing the spirits of the present invention. Therefore, the scope of the present invention is by no means limited to the above descriptions and is only determined by the accompanying claims.

I claim:

1. An apparatus for detecting heart characteristics, comprising:
   a plurality of ECG detecting electrodes;
   a blood pressure (BP) sensor;
   a preamplifier circuit, whose inputs are connected respectively to said ECG detecting electrodes and said BP sensor, for providing parallel multiplex outputs of ECG and BP signals;
   an A/D convertor, whose inputs are connected to said parallel multiplex outputs of said preamplifier circuit, for converting said analog ECG and BP signals into digital data;
   a data processing unit, whose inputs are connected to the digital output of said A/D convertor, for processing said digital data to generate stimulating instructions and to identify waveforms of said ECG and BP signals;
   a stimulating signal generating unit for generating heart stimulation signals under the control of said stimulating instructions issued by said data processing unit;
   two pairs of intracardiac electrodes, which are connected to the outputs of said stimulating signal generating unit, for applying said heart stimulation signals to atrium and ventricle, respectively; and
   an input-output device, which is connected to said data processing unit for inputting operating instructions therein and providing its processed results and identified waveforms as output;
   wherein said data processing unit includes means for processing the ECG and BP signals detected by said ECG detecting electrodes and BP sensor, and for issuing instructions for heart stimulation to said stimulating signal generating unit according to said processed results, said stimulating signal generating unit generating stimulating signals of specific waveforms according to said instructions and applying said stimulating signals to atrium and ventricle, respectively, via said intracardiac electrodes, said data processing unit including means for identifying the change of ECG and BP waveforms under the effects of the stimulating signals, for issuing instructions for stopping stimulation to said stimulating signal generating unit upon the identification of ME (NST) or VT waveforms, and for providing the identified waveforms and the amplitude of the stimulating signal which induces said waveforms to said input-output device.

2. An apparatus for detecting heart characteristics as claimed by claim 1, wherein said data processing unit comprises:
   a memory unit, whose input is connected to the output of said A/D convertor, for storing digital ECG and BP waveform signals;
   an ECG measuring unit which fetches selectively the ECG signals from said memory unit and measures the characteristics of the ECG signals;
   a BP measuring unit which fetches selectively the BP signals from said memory unit and measures the waveform and the diastolic BP value of the BP signals;
   an identification unit which inputs said ECG characteristics from said ECG measuring unit and said BP waveform and diastolic value from said BP measuring unit; and
   a calculating unit which inputs as its initial values said ECG characteristics from said ECG measuring unit and said BP waveform and diastolic value from said BP measuring unit, generates heart stimulating control signals under the control of said identification unit and provides said control signals to said stimulating signal generating unit;
   wherein said identification unit causes said calculating unit to issue said heart stimulating control signals according to identified ECG and BP waveforms, identifies the change of ECG and BP waveforms in response to the stimulating signals, so as to identify ME or VT waveforms, issues instructions for stopping stimulation to said calculating unit upon the identification of ME or VT waveforms and provides the identified waveforms and the amplitude of the stimulating pulse which induces said waveforms to said input-output device for displaying.

3. An apparatus for detecting heart characteristics as claimed in claim 2, wherein said stimulating signal generating unit generates, under the control of said calculating unit, said heart stimulating signals which comprises:
   a pacing pulse train to be applied to atrium with a period equal to 50-80% of the R—R interval measured by said ECG measuring unit, and an amplitude in the range of 1-20 mA; and
   an inducing pulse train to be applied to ventricle which is made up of a plurality of bursts of n pulses generated at such times that, after each group of N pacing pulses, a burst of inducing pulses is applied to the ventricle in the range between the start point and peak point of T wave, N being in the range of 1-10, the pulse period within each burst being in the range 4-10 ms, and n being determined according to said pulse period and the time from the start point of T wave to its peak point; wherein the amplitude of the inducing pulse burst is substantially 0.1 mA at beginning and is increased by about 0.1 mA for each burst until ME or VT is induced.

4. An apparatus for detecting heart characteristics as claimed in claim 2, wherein said stimulating signal generating unit generates, under the control of said calculating unit, said heart stimulating signals which comprises:
   a pacing pulse train to be applied to atrium with a period equal to 50-80% of the R—R interval measured by said ECG measuring unit, and an amplitude in the range of 1-20 mA; and
   an inducing pulse train to be applied to ventricle in a way that each inducing pulse is applied after N pacing pulses, wherein N is selected in the range of 1-10, the first inducing pulse is applied at the start point of T wave, and the following inducing pulses are each delayed 4-10 mS after each group of N pacing pulses, the amplitude of the inducing pulses is substantially 0.1 mA at first, wherein each inducing pulse is delayed relative to the preceding group of N pacing pulses by an amount greater than the amount of delay for the preceding inducing pulse until reaching the peak point of T wave, wherein the amplitude is increased by an increment of about 0.1 mA, and wherein the pulse is again applied at the start point of T wave for another cycle until ME or VT is induced.

5. An apparatus for detecting heart characteristics as claimed by claim 2, wherein said stimulating signal generating unit generates, under the control of said calculating unit, said heart stimulating signals which comprises:

a pacing pulse train to be applied to atrium with a period equal to 50-80% of the R—R interval measured by said ECG measuring unit and an amplitude in the range of 1-20 mA; and an inducing pulse train to be applied to ventricle in a way that each inducing pulse is applied after N pacing pulses, wherein N is selected in the range of 1-10, the first inducing pulse is applied at the peak point of T wave and the following pulses are each delayed by about 4-10 mS after each group of N pacing pulses, the amplitude of the inducing pulses is about 0.1 mA at first, wherein each pulse is delayed relative to the preceding group of N pacing pulses by an amount less than the amount of delay for the preceding inducing pulse until reaching the start point of T wave, wherein the amplitude is increased by an increment of about 0.1 mA and wherein the pulse is again applied at the peak point of T wave for another cycle until ME or VT is induced.

6. An apparatus for detecting heart characteristics as claimed by claim 2, wherein said identification unit receives as inputs from said ECG measuring unit and BP measuring unit the ECG and BP waveform data measured when the heart is stimulated, compares the BP waveform data detected at the time when an inducing pulse is applied to ventricle with the diastolic BP value detected at the time when pacing pulses are applied to atrium, so as to find out the time duration when said BP waveform is lower than said diastolic BP value; identifies the anomalous ECG waveform as ME or VT from the length of said duration, and then issues instruction for stopping stimulation, wherein said calculating unit, upon the identification of said ME or VT, fetches from said calculating unit the ampliitude of the inducing pulse which induces said waveform, so as to display the identified anamalous waveform and said inducing pulse amplitude via said input-output device.

7. An apparatus for detecting heart characteristics, comprising:

a plurality of ECG detecting electrodes;

a preamplifier circuit, whose inputs are connected to said ECG detecting electrodes, for providing ECG output;

an A/D convertor for converting said ECG output into digital data;

a data processing unit, whose input is connected to the digital output of said A/D convertor, for processing said digital data;

an input-output device connected to said data processing unit for inputting operating instructions and information thereto and providing the processed results and identified waveforms therefrom as output;

two pairs of dual path intracardiac electrodes for applying said heart stimulation signals to atrium and ventricle, respectively;

a stimulating signal generating unit having outputs connected to the dual-path heart stimulating electrodes; and an earth-floating circuit connected between said preamplifier circuit and said A/D convertor, for preventing electric interference on the ECG signals detected by said preamplifier circuit when the stimulating pulses are applied to heart by said stimulating signal generating unit;

wherein, said data processing unit includes means for processing ECG signals detected via said ECG detecting electrodes, for issuing heart stimulation instructions to said stimulating signal generating unit according to the processed results, said stimulating signal generating unit generating stimulating signals of specific pulse structure according to the information provided by said instructions and applying said stimulating signals to atrium and ventricle respectively via said heart stimulating electrodes; said data processing unit including means for identifying the waveform of PVC, ME or VT in ECG signals under the effects of said stimulating signals, for issuing instructions for stopping heart stimulation to said stimulating signal generating unit upon the identification of said waveform, and for providing the identified waveform and the amplitude of the pulse which induces said waveform to said input-output device as output.

8. The apparatus of claim 7, wherein said data processing unit further comprises:

a memory unit, whose input is connected to the output of said A/D convertor, for storing said digitized ECG signals;

an ECG measuring unit for fetching ECG signals from said memory unit and measuring parameters therefrom;

an identification unit for identifying the data inputted from said ECG measuring unit; and a calculating unit which inputs said parameters from said ECG measuring unit as initial vallues, generates heart stimulating control signals under the control of said identification unit, and issues said control signals to said stimulating signal generating unit;

wherein, said identification unit, according to identified ECG signals, controls said calculating unit to issue said heart stimulating control signals, identifies for ME or VT the ECG waveforms detected when the heart stimulating signals are applied, and upon the identifying of ME or VT waveform, issues instructions to said calculating unit for stopping heart stimulation and at the same time provides the identified ECG waveform and the amplitude of the stimulating pulse which induces said waveform to said input-output device for displaying.

9. The apparatus of claim 8, wherein said heart stimulating signals generated by said stimulating signal generating unit under the control of said calculating unit comprises:

a pacing pulse train to be applied to atrium, with a period Tso less than the R—R interval of the ECG signal detected before heart stimulation; and an inducing pulse train to be applied to ventricle for inducing ME or VT waveforms in ECG signals by adjusting the time location and amplitude of the inducing pulse relative to said pacing pulse;

wherein said identification unit receives the measured ECG data detected during the heart stimulating process from said ECG measuring unit, counts the number of successive anomalous heart beats having R—R interval less than said pacing period Tso, judges ME or VT according to said counted number and at the same time issues instructions to said calculating unit for stopping heart stimulation.

10. The apparatus of claim 9, wherein said identification unit identifies the number of successive anomalous waveforms caused by heart stimulation, and identifies said waveforms as ME or NST when said number is in the range of 3-9, 3 and 9 included, and wherein the calculating unit calculates the ventricular fibrillation threshold VFT from the amplitude MET of the ME's inducing pulse and according to the equation:

VFT=1.7932+1.0816 MET; and wherein said identification unit identifies the waveforms as VT and VFT when said number is equal to or greater than 10, wherein the calculating unit calculates the amplitude VTT of the VT's inducing pulse according to the equation:

VFT=0.1349+1.1608 VTT, and wherein the calculating unit provides the calculated VFT to said input-output device.

11. A method for detecting heart characteristics, comprising the steps of:
a. detecting ECG and BP waveforms via ECG detecting electrodes and a BP sensor;
b. measuring R—R interval, Q-T interval, shift of ST segment from detected ECG signals and calculating the diastolic BP values from detected BP signals;
c. applying via intracardiac electrodes, a pacing pulse train to right atrium, with the period of said pacing pulse being 50-80% of said R—R interval and the amplitude being in the range of 1-20 mA;
d. applying via intracardiac electrodes, an inducing pulse to right ventricle after each group of N pacing pulses with the amplitude of said inducing pulse being less than 0.2 mA and preferably 0.1 mA, and applying said inducing pulse within the range from the start point to the peak point of T wave, wherein N is in the range of 1-10;
e. detecting, when said inducing pulse is applied, whether the BP waveform is lower than said diastolic BP value and the duration of the BP decrease; wherein step d is repeated when no BP decrease is detected with the location of said inducing pulse being delayed 4-10 mS relative to the start point, within the range from the start point to the peak point of T wave, until the whole range is scanned;
f. increasing the amplitude of said inducing pulse by an increment of about 0.1 mA and repeating the above steps d and e, until detected BP value is lower than said diastolic BP value for the time duration longer than a predetermined value;
g. stopping the application of said pacing and inducing pulses to the heart and providing via output device the ECG waveforms corresponding to said BP decrease and the amplitude of the inducing pulse which induces said waveform for display.

12. The method of claim 11, wherein:
said step d is performed by applying, via said intracardiac electrodes, an inducing pulse burst of n pulses to right ventricle to scan the range from the start point to the peak point of T wave, the period of the pulse within the burst is 4-10 mS, said number n being determined by the period and the width of said range, and where the amplitude of the pulse is less than 0.2 mA, and wherein in said step e, when no BP decrease is detected, the amplitude of the pulse burst is increased by about 0.1 mA, the stimulating process being repeated until the BP signal detected is at a value less than said diastolic BP value for a time duration greater than a predetermined value.

13. the method of claim 11, further comprising the steps of:

h. measuring the ECG signals provided by step g, and identifying the signals as ME when the number of the wide and distorted QRS complex is 1-9, QRS duration being greater than 0.12S, and identifying the signals as VT when said number of the wide and distorted QRS complex is equal to or greater than 10, and terming the amplitude of the inducing pulse the threshold MET or VTT correspondingly.

14. The method of claim 13, further comprising the step of:
i. calculating threshold VFT when no shift of ST segment is measured by step b, using the equations:

VFT=2.4709+0.922 MET

VFT=0.3617+1.1137 VTT and calculating threshold VFT when shift of ST segment is measured by step b, using the equations:

VFT=0.0082+1.3995 MET

VFT=0.3209+1.0161 VTT and providing said VFT as output.

15. A method for detecting heart characteristics comprising the steps of:
a. detecting ECG signals by ECG detecting electrodes;
b. measuring the R—R interval and Q-T interval of the detected ECG signals;
c. applying, via stimulating electrodes, a pacing pulse train to atrium with a period Tso being 50-80% of said R—R interval and an amplitude being 1-20 mA;
d. applying, via the other stimulating electrodes, an inducing pulse train to ventricle to induce ME or VT waveforms by adjusting the time location and amplitude of said inducing pulses relative to said pacing pulses;
e. identifying the anomalous heart beats having R—R interval less than said pacing period Tso induced by said inducing pulses and repeating step d until said anomalous heart beats are induced; and
f. stopping the application of said pacing pulse train to atrium and said inducing pulse train to ventricle upon the identification of said anomalous heart beats, and providing the waveforms of said anomalous heart beats and the amplitude of the inducing pulse which induces said waveforms to output device for display.

16. The method of claim 15, further comprising the step of:
g. identifying the ECG waveform as ME or MST when the number of successive anomalous heart beats is 3-9, 3 and 9 included, and the amplitude of the inducing pulse as MET; and calculating VFT by equation:

VFT=1.7932+1.0816 MET;

identifying the ECG waveform as VT when the number of successive anomalous heart beats is equal to or greater than 10, and the amplitude of the inducing pulse as VTT, and calculating VFT by equation:

VFT=0.1349+1.1608 VTT; and i. providing said VFT for output.

17. The method of claim 16, further comprising terming as PVC the number of the anomalous heart beats when said number measured by step g is 1 or 2, and determining a vulnerable period of about 20 mS in width centered substantially at the location of the inducing pulse of said PVC; and returning to step d, and adjusting the location and amplitude of said inducing pulses within said vulnerable period until ME or VT is induced.

18. The method of claim 15, wherein the identification of the anomalous heart beats performed by step e comprises the following steps:

e1. filtering said detected ECG signals to eliminate the waveforms having a width less than about 10 mS;

e2. searching the filtered ECG signals to find the waveforms having a base frequency of 17 Hz, so as to identify each QRS complex; and e3. measuring the R—R interval of the identified QRS complex to find out the anomalous heart beats having R—R interval less than said pacing period Tso.

* * * * *

UNITED STATES PATENT AND TRADEMARK OFFICE
CERTIFICATE OF CORRECTION

PATENT NO. : 4,870,974
DATED : OCTOBERR 3, 1989
INVENTOR(S) : XIANGSHENG WANG

It is certified that error appears in the above-identified patent and that said Letters Patent is hereby corrected as shown below:

Column 21, line 37, in Claim 6: replace "anamalous" with --anomalous--

Column 22, line 29, in Claim 8: replace "vallues" with --values--

Column 23, line 44, in Claim 11: replace "untl" with --until--

Signed and Sealed this

Second Day of October, 1990

Attest:

HARRY F. MANBECK, JR.

*Attesting Officer*    *Commissioner of Patents and Trademarks*